United States Patent
Rotem et al.

(10) Patent No.: US 9,457,158 B2
(45) Date of Patent: Oct. 4, 2016

(54) AIR TRAP FOR INTRAVENOUS PUMP

(75) Inventors: Shachar Rotem, Kibbutz Metzer (IL);
Boaz Eitan, Hofit (IL); Shaul Eitan,
Hofit (IL); Omer Havron, Tel Aviv (IL)

(73) Assignee: Q-CORE MEDICAL LTD., Netanya (IL)

( * ) Notice: Subject to any disclaimer, the term of this patent is extended or adjusted under 35 U.S.C. 154(b) by 0 days.

(21) Appl. No.: 13/640,519

(22) PCT Filed: Apr. 12, 2011

(86) PCT No.: PCT/IB2011/051586
§ 371 (c)(1),
(2), (4) Date: Jan. 15, 2013

(87) PCT Pub. No.: WO2011/128850
PCT Pub. Date: Oct. 20, 2011

(65) Prior Publication Data
US 2013/0116620 A1   May 9, 2013

Related U.S. Application Data

(60) Provisional application No. 61/282,858, filed on Apr. 12, 2010.

(51) Int. Cl.
*A61M 5/36* (2006.01)
*A61M 5/142* (2006.01)
*A61M 5/14* (2006.01)

(52) U.S. Cl.
CPC .............. *A61M 5/36* (2013.01); *A61M 5/142* (2013.01); *A61M 5/1413* (2013.01); *A61M 5/365* (2013.01); *A61M 2205/6054* (2013.01)

(58) Field of Classification Search
CPC .................. A61M 5/142–5/1428; A61M 5/36
USPC ........................ 604/122, 123, 131
See application file for complete search history.

(56) References Cited

U.S. PATENT DOCUMENTS

| | | |
|---|---|---|
| 2,056,322 A | 10/1936 | Hoppe |
| 2,393,838 A | 1/1946 | Tarbox |

(Continued)

FOREIGN PATENT DOCUMENTS

| | | |
|---|---|---|
| DE | 10118086 A1 | 7/2002 |
| EP | 0215249 A1 | 3/1987 |

(Continued)

OTHER PUBLICATIONS

Honeywell Sensing and Control, "FSSI500NSB force sensor", Golden Valley, Minnesota, USA, 1998-2004 http://sccatalog.honeywell.com/imc/printfriendly.asp?FAM~force&PN-FSSI500NSB (5 pages).

(Continued)

*Primary Examiner* — Theodore Stigell
*Assistant Examiner* — Benjamin Koo
(74) *Attorney, Agent, or Firm* — Vladimir Sherman; Professional Patent Solutions

(57) ABSTRACT

An intravenous pump system includes an intravenous pump having an air bubble detector, a separate air trap module and a patient line. The air trap module is connectable to a set interface upon which the pump can operate. The air trap module includes an air chamber capable of receiving fluids and air, a plurality of valves controlling the flow of the fluids and air, and an air vent. The patient line is connectable to the air trap module and to a patient. The air trap module includes an actuator to control the state of the valves to enable, at least during a venting mode, the pump to push air out of the air chamber via the vent without disconnecting the patient from the patient line.

20 Claims, 19 Drawing Sheets

(56) References Cited

U.S. PATENT DOCUMENTS

| | | | |
|---|---|---|---|
| 2,743,898 A | 5/1956 | King | |
| 2,981,115 A | 4/1961 | Beguin | |
| 3,443,585 A | 5/1969 | Reinicke | |
| 3,511,583 A | 5/1970 | Brown | |
| 3,677,667 A | 7/1972 | Morrison | |
| 3,778,195 A | 12/1973 | Bamberg | |
| 3,982,722 A | 9/1976 | Bernard | |
| 3,982,725 A | 9/1976 | Clark | |
| 4,014,318 A | 3/1977 | Dockum et al. | |
| 4,039,269 A | 8/1977 | Pickering | |
| 4,155,362 A | 5/1979 | Jess | |
| 4,178,138 A | 12/1979 | Iles | |
| 4,236,880 A | 12/1980 | Archibald | |
| 4,270,532 A | 6/1981 | Franetzki et al. | |
| 4,290,346 A | 9/1981 | Bujan | |
| 4,320,781 A | 3/1982 | Bouvet et al. | |
| 4,373,525 A | 2/1983 | Kobayashi | |
| 4,450,375 A | 5/1984 | Siegal | |
| 4,479,797 A | 10/1984 | Kobayashi et al. | |
| 4,489,863 A | 12/1984 | Horchos et al. | |
| 4,493,706 A | 1/1985 | Borsanyi et al. | |
| 4,650,469 A | 3/1987 | Berg et al. | |
| 4,671,792 A | 6/1987 | Borsanyi | |
| 4,682,135 A | 7/1987 | Yamakawa | |
| 4,690,673 A | 9/1987 | Bloomquist | |
| 4,725,205 A | 2/1988 | Cannon et al. | |
| 4,728,265 A | 3/1988 | Cannon | |
| 4,741,736 A | 5/1988 | Brown | |
| 4,748,003 A | 5/1988 | Riley | |
| 4,755,168 A | 7/1988 | Romanelli et al. | |
| 4,836,752 A | 6/1989 | Burkett | |
| 4,867,744 A | 9/1989 | Borsanyi | |
| 4,893,991 A | 1/1990 | Heminway et al. | |
| 4,927,411 A | 5/1990 | Pastrone et al. | |
| 4,954,046 A | 9/1990 | Irvin et al. | |
| 4,954,256 A | 9/1990 | Degen et al. | |
| 4,978,335 A | 12/1990 | Arthur, III | |
| 5,061,241 A * | 10/1991 | Stephens, Jr. | A61M 5/142 137/539 |
| 5,074,756 A | 12/1991 | Davis | |
| 5,078,683 A | 1/1992 | Sancoff et al. | |
| 5,088,904 A | 2/1992 | Okada | |
| 5,096,385 A | 3/1992 | Georgi et al. | |
| 5,103,211 A | 4/1992 | Daoud et al. | |
| 5,151,019 A | 9/1992 | Danby et al. | |
| 5,152,680 A | 10/1992 | Okada | |
| 5,165,874 A | 11/1992 | Sancoff et al. | |
| 5,213,483 A | 5/1993 | Flaherty et al. | |
| 5,219,327 A | 6/1993 | Okada | |
| 5,222,946 A | 6/1993 | Kamen | |
| 5,246,347 A | 9/1993 | Davis | |
| 5,257,978 A | 11/1993 | Haber et al. | |
| 5,286,176 A | 2/1994 | Bonin | |
| 5,290,158 A | 3/1994 | Okada | |
| 5,308,333 A | 5/1994 | Skakoon | |
| 5,338,157 A | 8/1994 | Blomquist | |
| 5,395,320 A | 3/1995 | Padda et al. | |
| 5,429,485 A | 7/1995 | Dodge | |
| 5,485,408 A | 1/1996 | Blomquist | |
| 5,499,969 A | 3/1996 | Beuchat et al. | |
| 5,509,439 A | 4/1996 | Tantardini | |
| 5,527,295 A | 6/1996 | Wing | |
| 5,542,826 A | 8/1996 | Warner | |
| 5,569,188 A | 10/1996 | Mackool | |
| 5,575,309 A | 11/1996 | Connell | |
| 5,575,631 A | 11/1996 | Jester | |
| 5,577,891 A | 11/1996 | Loughnane et al. | |
| 5,584,667 A | 12/1996 | Davis | |
| 5,593,134 A | 1/1997 | Steber et al. | |
| 5,601,420 A | 2/1997 | Warner et al. | |
| 5,628,619 A | 5/1997 | Wilson | |
| 5,658,250 A | 8/1997 | Blomquist et al. | |
| 5,658,252 A | 8/1997 | Johnson | |
| 5,660,529 A | 8/1997 | Hill | |
| 5,669,877 A | 9/1997 | Blomquist | |
| 5,683,233 A | 11/1997 | Moubayed et al. | |
| 5,695,473 A | 12/1997 | Olsen | |
| 5,704,584 A | 1/1998 | Winterer et al. | |
| 5,742,519 A | 4/1998 | McClendon et al. | |
| 5,782,805 A | 7/1998 | Meinzer et al. | |
| 5,788,669 A | 8/1998 | Peterson | |
| 5,791,880 A | 8/1998 | Wilson | |
| 5,791,881 A | 8/1998 | Moubayed et al. | |
| 5,803,712 A | 9/1998 | Davis et al. | |
| 5,807,322 A | 9/1998 | Lindsey et al. | |
| 5,810,323 A | 9/1998 | Winterer et al. | |
| 5,853,386 A | 12/1998 | Davis et al. | |
| 5,876,370 A | 3/1999 | Blomquist | |
| 5,888,052 A | 3/1999 | Hill | |
| 5,896,076 A | 4/1999 | Van Namen | |
| 5,909,724 A | 6/1999 | Nishimura et al. | |
| 5,924,852 A | 7/1999 | Moubayed et al. | |
| 5,935,099 A | 8/1999 | Peterson et al. | |
| 5,935,106 A | 8/1999 | Olsen | |
| 5,943,633 A | 8/1999 | Wilson et al. | |
| 5,954,485 A | 9/1999 | Johnson et al. | |
| 5,980,490 A | 11/1999 | Tsoukalis | |
| 5,996,964 A | 12/1999 | Ben-Shalom | |
| 6,024,539 A | 2/2000 | Blomquist | |
| 6,095,189 A | 8/2000 | Ben-Shalom | |
| 6,110,153 A | 8/2000 | Davis et al. | |
| 6,146,109 A | 11/2000 | Davis et al. | |
| 6,164,921 A | 12/2000 | Moubayed et al. | |
| 6,165,874 A | 12/2000 | Powell et al. | |
| RE37,074 E | 2/2001 | Danby et al. | |
| 6,203,296 B1 | 3/2001 | Ray et al. | |
| 6,213,723 B1 | 4/2001 | Danby et al. | |
| 6,213,739 B1 | 4/2001 | Phallen et al. | |
| 6,234,773 B1 | 5/2001 | Hill et al. | |
| 6,241,704 B1 | 6/2001 | Peterson et al. | |
| 6,261,262 B1 | 7/2001 | Briggs et al. | |
| 6,280,408 B1 | 8/2001 | Sipin | |
| 6,312,227 B1 | 11/2001 | Davis | |
| 6,339,410 B1 | 1/2002 | Milner et al. | |
| 6,347,553 B1 | 2/2002 | Morris et al. | |
| 6,371,732 B1 | 4/2002 | Moubayed et al. | |
| 6,422,057 B1 | 7/2002 | Anderson | |
| 6,450,773 B1 | 9/2002 | Upton | |
| 6,475,180 B2 | 11/2002 | Peterson et al. | |
| 6,519,569 B1 | 2/2003 | White et al. | |
| 6,537,244 B2 | 3/2003 | Paukovits et al. | |
| 6,544,171 B2 | 4/2003 | Beetz et al. | |
| 6,558,347 B1 | 5/2003 | Jhuboo et al. | |
| 6,572,604 B1 | 6/2003 | Platt et al. | |
| 6,622,542 B2 | 9/2003 | Derek et al. | |
| 6,648,861 B2 | 11/2003 | Platt et al. | |
| 6,692,241 B2 | 2/2004 | Watanabe et al. | |
| 6,733,476 B2 | 5/2004 | Christenson et al. | |
| 6,742,992 B2 | 6/2004 | Davis | |
| 6,749,587 B2 | 6/2004 | Flaherty | |
| 6,768,425 B2 | 7/2004 | Flaherty et al. | |
| 6,788,199 B2 | 9/2004 | Crabtree et al. | |
| 6,790,198 B1 | 9/2004 | White et al. | |
| 6,902,549 B2 | 6/2005 | Marmaropoulos et al. | |
| 6,942,473 B2 | 9/2005 | Abrahamson et al. | |
| 7,018,361 B2 | 3/2006 | Gillespie, Jr. et al. | |
| 7,022,075 B2 | 4/2006 | Grunwald et al. | |
| 7,048,720 B1 | 5/2006 | Thorne, Jr. et al. | |
| 7,059,840 B2 | 6/2006 | Corwin et al. | |
| 7,122,026 B2 | 10/2006 | Rogers et al. | |
| 7,131,966 B1 | 11/2006 | Tamari | |
| 7,163,385 B2 | 1/2007 | Gharib et al. | |
| 7,347,836 B2 | 3/2008 | Peterson et al. | |
| 7,525,432 B2 | 4/2009 | Jackson | |
| 7,556,481 B2 | 7/2009 | Moubayed | |
| 7,645,258 B2 | 1/2010 | White et al. | |
| 7,654,976 B2 | 2/2010 | Peterson et al. | |
| 7,695,255 B2 | 4/2010 | Ben-Shalom et al. | |
| 7,698,156 B2 | 4/2010 | Martucci et al. | |
| 7,704,227 B2 | 4/2010 | Moberg et al. | |
| 7,762,795 B2 | 7/2010 | Moubayed | |
| 7,840,260 B2 | 11/2010 | Epley | |
| 7,892,332 B2 * | 2/2011 | Prisco et al. | 96/204 |
| 7,896,834 B2 | 3/2011 | Smisson, III et al. | |

(56) References Cited

U.S. PATENT DOCUMENTS

| | | | |
|---|---|---|---|
| 7,935,102 B2 | 5/2011 | Breznock et al. | |
| 7,938,796 B2 | 5/2011 | Moubayed et al. | |
| 7,963,946 B2 | 6/2011 | Moubayed et al. | |
| 7,998,121 B2 | 8/2011 | Stringham | |
| 8,025,634 B1 | 9/2011 | Moubayed et al. | |
| 8,029,253 B2 | 10/2011 | Rotem et al. | |
| 8,142,400 B2 | 3/2012 | Rotem et al. | |
| 8,182,445 B2 | 5/2012 | Moubayed et al. | |
| 8,197,235 B2 | 6/2012 | Davis | |
| 8,214,231 B2 | 7/2012 | Martucci et al. | |
| 8,234,128 B2 | 7/2012 | Martucci et al. | |
| 8,241,018 B2 | 8/2012 | Harr | |
| 8,257,654 B2 | 9/2012 | Maus et al. | |
| 8,308,457 B2 | 11/2012 | Rotem et al. | |
| 8,334,768 B2 | 12/2012 | Eaton et al. | |
| 8,337,168 B2 | 12/2012 | Rotem et al. | |
| 8,343,111 B2 | 1/2013 | Beck et al. | |
| 8,352,290 B2 | 1/2013 | Bartz et al. | |
| 8,363,583 B2 | 1/2013 | Jia et al. | |
| 8,371,832 B2 | 2/2013 | Rotem et al. | |
| 8,444,587 B2 | 5/2013 | Kelly et al. | |
| 8,489,427 B2 | 7/2013 | Simpson et al. | |
| 8,535,025 B2 | 9/2013 | Rotem et al. | |
| 8,579,816 B2 | 11/2013 | Kamath et al. | |
| 8,666,367 B2 | 3/2014 | Sharp et al. | |
| 8,672,875 B2 | 3/2014 | Vanderveen et al. | |
| 8,678,793 B2 | 3/2014 | Goldor et al. | |
| 8,920,144 B2 | 12/2014 | Rotem et al. | |
| 9,056,160 B2 | 6/2015 | Rotem et al. | |
| 2001/0029321 A1 | 10/2001 | Beetz et al. | |
| 2002/0056675 A1 | 5/2002 | Hegde | |
| 2002/0094287 A1 | 7/2002 | Davis | |
| 2002/0156402 A1 | 10/2002 | Woog et al. | |
| 2002/0165503 A1 | 11/2002 | Morris et al. | |
| 2003/0034887 A1 | 2/2003 | Crabtree et al. | |
| 2003/0040700 A1 | 2/2003 | Hickle et al. | |
| 2003/0065536 A1 | 4/2003 | Hansen et al. | |
| 2003/0109988 A1 | 6/2003 | Geissler et al. | |
| 2003/0140928 A1 | 7/2003 | Bui et al. | |
| 2003/0141981 A1 | 7/2003 | Bui et al. | |
| 2003/0182586 A1 | 9/2003 | Numano | |
| 2004/0167804 A1 | 8/2004 | Simpson et al. | |
| 2004/0172222 A1 | 9/2004 | Simpson et al. | |
| 2004/0181314 A1 | 9/2004 | Zaleski | |
| 2004/0191112 A1 | 9/2004 | Hill et al. | |
| 2004/0204673 A1 | 10/2004 | Flaherty | |
| 2004/0204685 A1 | 10/2004 | Wright et al. | |
| 2004/0235446 A1 | 11/2004 | Flaherty et al. | |
| 2005/0001369 A1 | 1/2005 | Cross | |
| 2005/0022274 A1 | 1/2005 | Campbell et al. | |
| 2005/0055242 A1 | 3/2005 | Bello et al. | |
| 2005/0088409 A1 | 4/2005 | Van Berkel | |
| 2005/0112001 A1 | 5/2005 | Bahnen et al. | |
| 2005/0171501 A1* | 8/2005 | Kelly | 604/500 |
| 2005/0191196 A1 | 9/2005 | Tanner et al. | |
| 2005/0214146 A1 | 9/2005 | Corwin et al. | |
| 2006/0051218 A1 | 3/2006 | Harttig | |
| 2006/0083644 A1 | 4/2006 | Zumbrum et al. | |
| 2006/0173419 A1* | 8/2006 | Malcolm | 604/246 |
| 2006/0213249 A1 | 9/2006 | Uram et al. | |
| 2007/0032098 A1 | 2/2007 | Bowles et al. | |
| 2007/0048161 A1 | 3/2007 | Moubayed | |
| 2007/0060872 A1 | 3/2007 | Hall et al. | |
| 2007/0118405 A1 | 5/2007 | Campbell et al. | |
| 2007/0135866 A1 | 6/2007 | Baker et al. | |
| 2007/0154336 A1 | 7/2007 | Miyazaki et al. | |
| 2007/0217931 A1 | 9/2007 | Estes et al. | |
| 2007/0269324 A1 | 11/2007 | Goldor et al. | |
| 2008/0015506 A1 | 1/2008 | Davis | |
| 2008/0065007 A1 | 3/2008 | Peterson et al. | |
| 2008/0065016 A1 | 3/2008 | Peterson et al. | |
| 2008/0067462 A1 | 3/2008 | Miller et al. | |
| 2008/0071251 A1 | 3/2008 | Moubayed et al. | |
| 2008/0095649 A1 | 4/2008 | Ben-Shalom et al. | |
| 2008/0144560 A1 | 6/2008 | Jia et al. | |
| 2008/0145249 A1 | 6/2008 | Smisson et al. | |
| 2008/0146995 A1* | 6/2008 | Smisson et al. | 604/67 |
| 2008/0275307 A1 | 11/2008 | Poschmann | |
| 2009/0088675 A1 | 4/2009 | Kelly et al. | |
| 2009/0163864 A1 | 6/2009 | Breznock et al. | |
| 2009/0203329 A1 | 8/2009 | White et al. | |
| 2009/0221964 A1 | 9/2009 | Rotem et al. | |
| 2009/0240201 A1 | 9/2009 | Rotem et al. | |
| 2009/0270810 A1 | 10/2009 | DeBelser et al. | |
| 2009/0300507 A1 | 12/2009 | Raghavan et al. | |
| 2009/0317268 A1 | 12/2009 | Rotem et al. | |
| 2010/0016781 A1 | 1/2010 | Nakayama et al. | |
| 2010/0036322 A1 | 2/2010 | Rotem | |
| 2010/0082001 A1 | 4/2010 | Beck et al. | |
| 2010/0168545 A1 | 7/2010 | Kamath et al. | |
| 2010/0211002 A1 | 8/2010 | Davis | |
| 2010/0228223 A1* | 9/2010 | Williams et al. | 604/500 |
| 2010/0234708 A1 | 9/2010 | Buck et al. | |
| 2010/0279652 A1 | 11/2010 | Sharp et al. | |
| 2011/0148624 A1 | 6/2011 | Eaton et al. | |
| 2011/0152772 A1 | 6/2011 | Rotem et al. | |
| 2011/0152831 A1 | 6/2011 | Rotem et al. | |
| 2011/0167133 A1 | 7/2011 | Jain | |
| 2011/0251856 A1 | 10/2011 | Maus et al. | |
| 2011/0264043 A1 | 10/2011 | Kotnik et al. | |
| 2011/0276000 A1 | 11/2011 | Stringham | |
| 2011/0282291 A1 | 11/2011 | Ciccone | |
| 2011/0318208 A1 | 12/2011 | Goldor et al. | |
| 2012/0059389 A1 | 3/2012 | Larson et al. | |
| 2012/0062387 A1 | 3/2012 | Vik et al. | |
| 2012/0136305 A1 | 5/2012 | Gagliardoni et al. | |
| 2012/0241525 A1 | 9/2012 | Borges et al. | |
| 2013/0006666 A1 | 1/2013 | Schneider et al. | |
| 2013/0046508 A1 | 2/2013 | Sur et al. | |
| 2013/0116620 A1 | 5/2013 | Rotem et al. | |
| 2013/0116623 A1 | 5/2013 | Rotem et al. | |
| 2013/0142670 A1 | 6/2013 | Rotem et al. | |
| 2013/0209275 A1 | 8/2013 | Rotem et al. | |
| 2013/0279370 A1 | 10/2013 | Eitan et al. | |
| 2013/0345623 A1 | 12/2013 | Kopperschmidt et al. | |
| 2014/0005631 A1 | 1/2014 | Rotem et al. | |
| 2014/0119954 A1 | 5/2014 | Schweitzer et al. | |
| 2014/0197824 A1 | 7/2014 | Gillespie et al. | |
| 2014/0222377 A1 | 8/2014 | Bitan et al. | |
| 2014/0276564 A1 | 9/2014 | Schneider | |
| 2014/0369872 A1 | 12/2014 | Goldor et al. | |
| 2014/0378901 A1 | 12/2014 | Rotem et al. | |
| 2015/0038187 A1 | 2/2015 | Ho et al. | |
| 2015/0073338 A1 | 3/2015 | Waldhoff et al. | |
| 2015/0105726 A1 | 4/2015 | Qi et al. | |
| 2015/0137988 A1 | 5/2015 | Gravenstein et al. | |
| 2015/0141955 A1 | 5/2015 | Ruchti et al. | |
| 2015/0172921 A1 | 6/2015 | Wang et al. | |
| 2015/0182694 A1 | 7/2015 | Rosinko | |
| 2015/0192120 A1 | 7/2015 | Rotem et al. | |

FOREIGN PATENT DOCUMENTS

| | | |
|---|---|---|
| EP | 0225158 A2 | 6/1987 |
| EP | 0315312 A1 | 5/1989 |
| EP | 0429866 A1 | 6/1991 |
| EP | 0483794 A1 | 5/1992 |
| EP | 0858812 A2 | 8/1998 |
| EP | 1031358 A1 | 8/2000 |
| EP | 1350955 A2 | 10/2003 |
| EP | 1557186 | 7/2005 |
| EP | 1611834 A2 | 1/2006 |
| EP | 1485149 B1 | 7/2008 |
| FR | 2632529 A1 | 12/1989 |
| FR | 2753236 A1 | 3/1998 |
| JP | 60043188 A | 3/1985 |
| JP | 6-169992 A | 6/1994 |
| JP | 2002-57738 A | 2/2002 |
| JP | 2004141418 A | 5/2004 |
| WO | 8400691 A1 | 3/1984 |
| WO | 9116933 A1 | 11/1991 |
| WO | 9325816 A1 | 12/1993 |
| WO | 9408647 A1 | 4/1994 |
| WO | 9603168 A1 | 2/1996 |

(56) References Cited

FOREIGN PATENT DOCUMENTS

| WO | 9630679 | A1 | 10/1996 |
|---|---|---|---|
| WO | 9734084 | A1 | 9/1997 |
| WO | 9804301 | A1 | 2/1998 |
| WO | 9813080 | A2 | 4/1998 |
| WO | 9847551 | A1 | 10/1998 |
| WO | 99/58178 | A1 | 11/1999 |
| WO | 0139816 | A2 | 6/2001 |
| WO | 0165232 | A1 | 9/2001 |
| WO | 0236044 | A2 | 5/2002 |
| WO | 0238204 | A2 | 5/2002 |
| WO | 0249509 | A2 | 6/2002 |
| WO | 02068015 | A2 | 9/2002 |
| WO | 03027503 | A1 | 4/2003 |
| WO | 03080158 | A1 | 10/2003 |
| WO | 2004070548 | A2 | 8/2004 |
| WO | 2004093648 | A2 | 11/2004 |
| WO | 2005089263 | A2 | 9/2005 |
| WO | 2006/056986 | A1 | 6/2006 |
| WO | 2007133259 | A1 | 11/2007 |
| WO | 2008036658 | A2 | 3/2008 |
| WO | 2008059492 | A2 | 5/2008 |
| WO | 2008059493 | A2 | 5/2008 |
| WO | 2008059494 | A2 | 5/2008 |
| WO | 2008059495 | A2 | 5/2008 |
| WO | 2008059496 | A2 | 5/2008 |
| WO | 2008059498 | A2 | 5/2008 |
| WO | 2008059499 | A2 | 5/2008 |
| WO | 2008130644 | A1 | 10/2008 |
| WO | 2010053702 | A1 | 5/2010 |
| WO | 2010053703 | A1 | 5/2010 |
| WO | 2010091313 | A2 | 8/2010 |
| WO | 2011128850 | A2 | 10/2011 |
| WO | 2012095827 | A1 | 7/2012 |
| WO | 2012095829 | A2 | 7/2012 |
| WO | 2013001425 | A2 | 1/2013 |
| WO | 2013/028704 | A1 | 2/2013 |
| WO | 2013/090748 | A1 | 6/2013 |

OTHER PUBLICATIONS

International Application PCT/IL2007/001398 Search Report dated Jun. 11, 2008 (2 pages).
International Application PCT/IL2007/001398 Patentability Report dated May 19, 2009 (6 pages).
International Application PCT/IL2007/001399 Search Report dated Jun. 4, 2008 (3 pages).
International Application PCT/IL2007/001399 Patentability Report dated May 19, 2009 (9 pages).
International Application PCT/IL2007/001400 Search Report dated Jul. 15, 2008 (3 pages).
International Application PCT/IL2007/001400 Patentability Report dated May 19, 2009 (10 pages).
International Application PCT/IL2007/001401 Search Report dated Sep. 24, 2008 (2 pages).
International Application PCT/IL2007/001401 Patentability Report dated May 19, 2009 (11 pages).
International Application PCT/IL2007/001402 Search Report dated Jun. 20, 2008 (3 pages).
International Application PCT/IL2007/001402 Patentability Report dated May 19, 2009 (4 pages).
International Application PCT/IL2007/001404 Search Report dated Jul. 14, 2008 (2 pages).
International Application PCT/IL2007/001404 Patentability Report dated May 19, 2009 (7 pages).
International Application PCT/IL2007/001405 Search Report dated Jul. 21, 2008 (4 pages).
International Application PCT/IL2007/001405 Patentability Report dated May 19, 2009 (7 pages).
International Application PCT/IL2005/001249 Search Report dated Apr. 5, 2006 (18 pages).
International Application PCT/IL1997/000289 Search report dated Jan. 27, 1998 (18 pages).
International Application PCT/IL1997/000290 Search Report dated Jan. 27, 1998 (18 pages).
International Application PCT/IL2003/000947 Search Report dated Mar. 3, 2004 (43 pages).
International Application PCT/IB2011/051586 Search Report dated Oct. 27, 2011 (3 pages).
International Application PCT/IB2011/051586 Patentability Report dated Oct. 16, 2012 (9 pages).
International Application PCT/IB2012/050192 Search Report dated Aug. 17, 2012 (2 pages).
International Application PCT/IB2012/050192 Patentability Report dated Jul. 16, 2013 (6 pages).
International Application PCT/IB2012/050189 Search Report dated May 30, 2012 (2 pages).
International Application PCT/IB2012/050189 Patentability Report dated Jul. 16, 2013 (5 pages).
International Application PCT/IB2012/053149 Search Report dated Jan. 15, 2013 (2 pages).
U.S. Appl. No. 09/125,438 Official Action dated May 3, 1999 (4 pages).
U.S. Appl. No. 09/125,438 Official Action dated Jul. 15, 1999 (7 pages).
U.S. Appl. No. 10/535,103 Official Action dated Feb. 2, 2009 (9 pages).
European Application No. 05810500.8 Official Action dated Jul. 6, 2009 (5 pages).
European Application No. 05810500.8 Response to Official Action dated Jul. 6, 2009, submitted Oct. 15, 2009 (8 pages).
European Application No. 05810500.8 Official Action dated Jan. 23, 2012 (4 pages).
European Application No. 05810500.8 Response to Official Action dated Jan. 23, 2012, submitted May 22, 2012 (6 pages).
U.S. Appl. No. 11/791,599 Official Action (Non-Final) dated Aug. 19, 2010 (16 pages).
U.S. Appl. No. 11/791,599 Response to Official Action (Non-Final) dated Aug. 19, 2010, submitted Jan. 11, 2011 (8 pages).
U.S. Appl. No. 11/791,599 Official Action (Final) dated Mar. 31, 2011 (13 pages).
U.S. Appl. No. 11/791,599 Response to Official Action (Final) dated Mar. 31, 2011, submitted May 23, 2011 (7 pages).
U.S. Appl. No. 11/791,599 Notice of Allowance issued Jun. 14, 2011 (5 pages).
U.S. Appl. No. 13/229,798 Official Action (Non-Final) dated Dec. 26, 2012 (10 pages).
U.S. Appl. No. 13/229,798 Response to Official Action (Non-Final) dated Dec. 26, 2012, submitted Mar. 21, 2013 (13 pages).
U.S. Appl. No. 13/229,798 Notice of Allowance issued Apr. 19, 2013 (6 pages).
U.S. Appl. No. 13/229,798 Notice of Withdrawal from Issue dated May 13, 2013 (1 page).
U.S. Appl. No. 13/229,798 Official Action (Non-Final) dated Jun. 21, 2013 (6 pages).
Chinese Patent Application No. 200580045471.3 "Finger-type peristaltic pump" Official Action dated Jul. 18, 2008 and English translation thereof (7 pages).
Chinese Patent Application No. 200780041966.8 Official Action dated Jul. 13, 2010 (7 pages).
Chinese Patent Application No. 200780041966.8 Response to Official Action dated Jul. 13, 2010, as submitted (6 pages).
Chinese Patent Application No. 200780041966.8, translation of Notification of Grant, issued Jan. 28, 2011 (2 pages).
U.S. Appl. No. 12/464,202 Official Action (Non-Final) dated Oct. 3, 2011 (7 pages).
U.S. Appl. No. 12/464,202 Response to Official Action (Non-Final) dated Oct. 3, 2011, submitted Feb. 12, 2012 (12 pages).
U.S. Appl. No. 12/464,202 Notice of Allowance issued Jul. 11, 2012 (5 pages).
U.S. Appl. No. 12/463,399 Official Action (Non-Final) dated Jul. 21, 2011 (15 pages).
U.S. Appl. No. 12/463,399 Response to Official Action (Non-Final) dated Jul. 21, 2011, submitted Oct. 21, 2011 (5 pages).

(56) References Cited

OTHER PUBLICATIONS

U.S. Appl. No. 12/463,399 Official Action (Final) dated Dec. 13, 2011 (7 pages).
U.S. Appl. No. 12/463,399 Response to Official Action (Final) dated Dec. 13, 2011, submitted Feb. 12, 2012 (10 pages).
U.S. Appl. No. 12/463,399 Advisory Action and Applicant Initiated Interview Summary dated Mar. 8, 2012 (8 pages).
U.S. Appl. No. 12/463,399 Response to Official Action (Final) dated Dec. 13, 2011, submitted Mar. 26, 2012 with Request for Continued Examination (13 pages).
U.S. Appl. No. 12/463,399 Notice of Allowance issued Apr. 29, 2013 (14 pages).
U.S. Appl. No. 12/514,310 Official Action (Non-Final) dated Jul. 21, 2011 (8 pages).
U.S. Appl. No. 12/514,310 Response to Official Action (Non-Final) dated Jul. 21, 2011, submitted Oct. 21, 2011 (8 pages).
U.S. Appl. No. 12/514,310 Official Action (Final) dated Jan. 20, 2012 (10 pages).
U.S. Appl. No. 12/514,310 Response to Official Action (Final) dated Jan. 20, 2012, submitted Apr. 25, 2012 with Request for Continued Examination (11 pages).
U.S. Appl. No. 12/514,310 Official Action (Non-Final) dated May 25, 2012 (7 pages).
U.S. Appl. No. 12/514,310 Response to Official Action (Non-Final) dated May 25, 2012, submitted Jun. 28, 2012 (6 pages).
U.S. Appl. No. 12/514,310 Notice of Allowance issued Aug. 22, 2012 (7 pages).
U.S. Appl. No. 12/514,311 Official Action (Non-Final) dated Sep. 16, 2010 (10 pages).
U.S. Appl. No. 12/514,311 Response to Official Action (Non-Final) dated Sep. 16, 2010, submitted Dec. 9, 2010 (23 pages).
U.S. Appl. No. 12/514,311 Official Action (Final) dated Feb. 18, 2011 (7 pages).
U.S. Appl. No. 12/514,311 Examiner Interview Summary Record dated Mar. 4, 2011 (4 pages).
U.S. Appl. No. 12/514,311 Response to Official Action (Final) dated Feb. 18, 2011, submitted Mar. 31, 2011 with Request for Continued Examination (9 pages).
European Patent Application No. 10192477.7 Search Report dated May 10, 2011 (5 pages).
European Patent Application No. 10192477.7 Response to Search Report dated May 10, 2011, submitted Dec. 28, 2011.
U.S. Appl. No. 12/644,026 Official Action (Non-Final) dated Apr. 6, 2012 (12 pages).
U.S. Appl. No. 12/644,026 Response to Official Action (Non-Final) dated Apr. 6, 2012, submitted Jul. 5, 2012 (11 pages).
U.S. Appl. No. 12/644,026 Notice of Allowance issued Oct. 11, 2012 (10 pages).
U.S. Appl. No. 13/742,454 Official Action (Non-Final) dated Oct. 7, 2013 (13 pages).
U.S. Appl. No. 12/644,027 Official Action (Non-Final) dated Apr. 28, 2011 (7 pages).
U.S. Appl. No. 12/644,027 Response to Official Action (Non-Final) dated Apr. 28, 2011, submitted Jul. 21, 2011 (10 pages).
U.S. Appl. No. 12/644,027 Notice of Allowance issued Nov. 17, 2011 (5 pages).
U.S. Appl. No. 13/229,798 Response to Official Action (Non-Final) dated Jun. 21, 2013, submitted Oct. 21, 2013 (3 pages).
U.S. Appl. No. 13/229,798 Notice of Allowance issued Nov. 14, 2013 (54 pages).
U.S. Appl. No. 13/651,420 Official Action (Non-Final) dated Nov. 4, 2013 (8 pages).
U.S. Appl. No. 13/651,420 Response to Official Action (Non-Final) dated Nov. 4, 2013, submitted Nov. 21, 2013 (2 pages).
U.S. Appl. No. 13/681,440 Official Action (Non-Final) dated Oct. 24, 2013 (11 pages).
U.S. Appl. No. 13/651,420 Official Action (Non-Final) dated Jan. 6, 2014 (8 pages).
U.S. Appl. No. 13/651,420 Response to Official Action (Non-Final) dated Jan. 6, 2014, submitted Mar. 5, 2014 (9 pages).
U.S. Appl. No. 13/651,420 Official Action (Final) dated Apr. 24, 2014 (8 pages).
U.S. Appl. No. 13/651,420 Response to Official Action (Final) dated Apr. 24, 2014, submitted Jul. 22, 2014 with Request for Continued Examination (15 pages).
U.S. Appl. No. 13/651,420 Official Action (Non-Final) dated Aug. 19, 2014 (10 pages).
U.S. Appl. No. 13/651,420 Response to Official Action (Non-Final) dated Aug. 19, 2014, submitted Dec. 18, 2014 (7 pages).
U.S. Appl. No. 14/016,105 Official Action (Non-Final) dated Oct. 15, 2014 (10 pages).
U.S. Appl. No. 13/681,440 Response to Official Action (Non-Final) dated Oct. 24, 2013, submitted Jan. 20, 2014 (10 pages).
U.S. Appl. No. 13/681,440 Official Action (Final) dated Feb. 14, 2014 (14 pages).
U.S. Appl. No. 13/681,440 Response to Official Action (Final) dated Feb. 14, 2014, submitted Jul. 14, 2014 with Request for Continued Examination (14 pages).
U.S. Appl. No. 13/681,440 Official Action (Non-Final) dated Sep. 2, 2014 (19 pages).
U.S. Appl. No. 12/514,311 Official Action (Non-Final) dated Oct. 7, 2014 (11 pages).
U.S. Appl. No. 13/742,454 Response to Official Action (Non-Final) dated Oct. 7, 2013, submitted Jan. 6, 2014 (7 pages).
U.S. Appl. No. 13/742,454 Official Action (Final) dated Mar. 28, 2014 (14 pages).
U.S. Appl. No. 13/742,454 Response to Official Action (Final) dated Mar. 28, 2014, submitted Jun. 29, 2014 with Request for Continued Examination (10 pages).
U.S. Appl. No. 13/742,454 Notice of Allowance issued Aug. 21, 2014 (10 pages).
U.S. Appl. No. 13/640,519 Official Action (Non-Final) dated Dec. 24, 2013 (7 pages).
U.S. Appl. No. 13/640,519 Response to Official Action (Non-Final) dated Dec. 24, 2013, submitted Jan. 16, 2014 (2 pages).
U.S. Appl. No. 13/640,519 Official Action (Non-Final) dated Mar. 20, 2014 (15 pages).
U.S. Appl. No. 13/640,519 Response to Official Action (Non-Final) dated Mar. 20, 2014, submitted Jun. 17, 2014 (14 pages).
U.S. Appl. No. 13/640,519 Official Action (Final) dated Oct. 1, 2014 (11 pages).
U.S. Appl. No. 13/924,572 Official Action (Non-Final) dated Dec. 2, 2014 (13 pages).
European Application No. 11768544.6 Supplementary Partial European Search Report dated Nov. 13, 2014 (7 pages).
European Application No. 12734200.4 Supplementary European Search Report dated Aug. 18, 2014 (6 pages).
European Application No. 05810500.8 Official Action dated Nov. 3, 2014 (5 pages).
European Application No. 05810500.8 Response to Official Action dated Nov. 3, 2014, submitted Mar. 9, 2015 (31 pages).
Indian Patent Application No. 2344KOLNP2007 Office Action dated Dec. 31, 2014 (2 pages).
Indian Patent Application No. 2344KOLNP2007 Response to Office Action dated Dec. 31, 2014, submitted Aug. 7, 2015 (19 pages).
U.S. Appl. No. 14/181,673 Official Action (Non-Final) dated Jun. 3, 2015 (12 pages).
U.S. Appl. No. 13/651,420 Official Action (Final) dated Mar. 16, 2015 (6 pages).
U.S. Appl. No. 13/651,420 Response to Official Action (Final) dated Mar. 16, 2015, submitted May 14, 2015 (5 pages).
U.S. Appl. No. 13/651,420 Official Action (Final) dated Jun. 9, 2015 (9 pages).
U.S. Appl. No. 14/016,105 Response to Official Action (Non-Final) dated Oct. 15, 2014, submitted Jan. 14, 2015 (7 pages).
U.S. Appl. No. 14/016,105 Notice of Allowance dated Feb. 17, 2015 (14 pages).
U.S. Appl. No. 13/681,440 Response to Official Action (Non-Final) dated Sep. 2, 2014, submitted Feb. 25, 2015 (12 pages).
U.S. Appl. No. 13/681,440 Official Action (Final) dated Apr. 24, 2015 (21 pages).
U.S. Appl. No. 12/514,311 Response to Official Action (Non-Final) dated Oct. 7, 2014, submitted Jan. 7, 2015 (5 pages).

(56) References Cited

OTHER PUBLICATIONS

U.S. Appl. No. 12/514,311 Official Action (Final) dated Apr. 20, 2015 (12 pages).
U.S. Appl. No. 12/514,311 Response to Official Action (Final) dated Apr. 20, 2015, submitted Jun. 21, 2015 (10 pages).
U.S. Appl. No. 12/514,311 Official Action (Advisory Action) dated Jul. 1, 2015 (8 pages).
U.S. Appl. No. 12/514,311 Response to Official Action (Advisory Action) dated Jul. 1, 2015, submitted Jul. 20, 2015 (8 pages).
U.S. Appl. No. 12/514,311 Official Action (Advisory Action) dated Aug. 5, 2015 (6 pages).
European Application No. 10192477.7 Official Action dated Jul. 6, 2015 (5 pages).
European Application No. 11768544.6 Response to Official Action dated Dec. 2, 2014, submitted May 29, 2015 (12 pages).
U.S. Appl. No. 13/640,519 Response to Official Action (Final) dated Oct. 1, 2014, submitted Dec. 28, 2014 (15 pages).
U.S. Appl. No. 13/640,519 Official Action (Non-Final) dated May 6, 2015 (13 pages).
European Application No. 12734200.4 Response to Official Communication dated Sep. 4, 2014, submitted Mar. 4, 2015 (16 pages).
U.S. Appl. No. 13/978,538 Official Action (Non-Final) dated Jan. 23, 2015 (24 pages).
U.S. Appl. No. 13/978,538 Response to Official Action (Non-Final) dated Jan. 23, 2015, submitted May 21, 2015 (13 pages).
U.S. Appl. No. 13/978,538 Official Action (Non-Final) dated Jul. 24, 2015 (16 pages).
European Application No. 12805094.5 Supplementary Partial European Search Report dated Feb. 23, 2015 (8 pages).
European Application No. 12805094.5 Response to Supplementary Partial European Search Report submitted Apr. 2, 2015 (1 page).
European Application No. 12805094.5 Supplementary European Search Report dated Jun. 30, 2015 (14 pages).
U.S. Appl. No. 13/924,572 Response to Official Action (Non-Final) dated Dec. 2, 2014, submitted Mar. 26, 2015 (11 pages).
U.S. Appl. No. 13/924,572 Official Action (Non-Final) dated May 14, 2015 (12 pages).
PCT Appl. No. PCT/IB14/62106 International Search Report and Written Opinion dated Feb. 24, 2015 (8 pages).
PCT Appl. No. PCT/IB15/50873 International Search Report and Written Opinion dated Jun. 25, 2015 (8 pages).

\* cited by examiner

AIR TRAP FOR INTRAVENOUS PUMP

CROSS-REFERENCE TO RELATED APPLICATIONS

This application claims benefit from U.S. Provisional Patent Application No. 61/282,858, filed Apr. 12, 2010, which is hereby incorporated in its entirety by reference.

FIELD OF THE INVENTION

The present invention relates to infusion pumps for medical treatments generally and to handling of air and air in the pump system in particular.

BACKGROUND OF THE INVENTION

An intravenous (IV) system typically includes a bag holding the fluids to be infused, tubes connecting the bag to the patient and a pump to regulate the flow of fluids into the patient. Such pumps are utilized for providing many types of fluid, chemotherapy being but one example.

The chemicals for chemotherapy are typically very expensive and very toxic. This requires that minimal amounts of the chemicals be wasted and that the medical staff, who are generally healthy, not be exposed to the toxic drugs. Unfortunately, current pump technology does not ensure this.

The problem is that the toxic fluids generate air as they move through the IV tubes and only a small amount of air may be introduced into a patient's bloodstream. Current pumps have an air bubble detector, to detect the presence of air (as an air bubble) and to stop the operation of the pump as a result of a small amount of air (for example, 1 ml) passing to the patient within a pre-defined period of time (such as 15 min) or single bubbles that are more than a pre-determined size (0.2 ml as an example). The pump then alerts the medical staff, which detaches the tubes, refills them with fluid (usually by spilling some of the fluid into a container of some kind) removing the air bubbles in the process and restarts the pump. Unfortunately, patients receiving chemotherapy are very sensitive to contamination, which may happen when the tubes are detached.

Moreover, this procedure can expose the medical staff to the toxic fluids and air and it spills the expensive drugs. Moreover, detaching the tubes exposes them and can lead to contamination of the patient. Another issue is that the air bubbles tend to stop treatment in short intervals.

The following patent publications discuss various attempts to solve these problems, including adding traps for air in the pump and after the pump: U.S. Pat. No. 7,131,966 to Tamari, U.S. Pat. No. 4,954,256 to Degen et al, US 2002/0056675 to Hegde, U.S. Pat. No. 6,280,408 to Sipin, U.S. Pat. No. 5,308,333 to Skakoon, U.S. Pat. No. 7,048,720 to Thorne, Jr. et al and U.S. Pat. No. 4,927,411 to Pastrone et al.

SUMMARY OF THE PRESENT INVENTION

There is therefore provided, in accordance with a preferred embodiment of the present invention, an intravenous pump system including an intravenous pump having an air bubble detector; a separate air trap module and a patient line. The air trap module is connectable to a set interface which is operatable upon by the intravenous pump. The air trap module includes an air chamber capable of receiving fluids and air, a plurality of valves controlling the flow of the fluids and air, and an air vent. The patient line is connectable to the air trap module and to a patient. The air trap module includes an actuator to control the state of the valves to enable, at least during a venting mode, the pump to push air out of the air chamber via the vent without disconnecting the patient from the patient line.

There is also provided, in accordance with a preferred embodiment of the present invention, an intravenous line including an air trap module at least connectable to a source of intravenous fluid, a set interface connectable to the air trap module and operatable upon by an intravenous pump, a return line connectable to the set interface and to the air trap module and a patient line connectable to the air trap module and to a patient.

Moreover, in accordance with a preferred embodiment of the present invention, the system includes a return line connectable to the set interface and to the air trap module.

Further, in accordance with a preferred embodiment of the present invention, at least during the venting mode, the pump pumps fluid through the return line and back into the air chamber.

Still further, in accordance with a preferred embodiment of the present invention, the valves include a venting valve at least to control the flow of air out of the air chamber, a patient valve controlling the patient line and a lower valve at least to control the flow of fluid from the air chamber to the set interface.

Moreover, in accordance with a preferred embodiment of the present invention, the venting valve is located generally at the top of the air trap module.

Additionally, in accordance with a preferred embodiment of the present invention, the air trap module includes a bypass path to pass incoming fluid to the set interface to be pumped into the air chamber via the return line when the venting valve is open.

Further, in accordance with a preferred embodiment of the present invention, the air chamber holds 2-4 ml.

Still further, in accordance with a preferred embodiment of the present invention, the actuator includes a unit to change the valves among a plurality of states.

Moreover, in accordance with a preferred embodiment of the present invention, one of the states is a treatment state during which at least the patient line valve is open, the venting valve is shut and the bypass path is closed. Another state is a priming state wherein the patient line valve is open, the venting valve is shut, the bypass path is closed and an upper fluid valve, near the top of the air chamber, is open. There may also be a sterilization state wherein all the valves are open.

Further, in accordance with a preferred embodiment of the present invention, the actuator may be either a manual dial or one or more electro mechanical actuators. For example, the electro mechanical actuators are controllable by the pump.

Still further, in accordance with a preferred embodiment of the present invention, the air detector of the pump detects the presence of air and controls the valves to change among treatment, venting and priming states accordingly.

Moreover, in accordance with a preferred embodiment of the present invention, there may be a unit to connect the air trap module upstream of the pump.

Alternatively, in accordance with a preferred embodiment of the present invention, the valves may alternatively include a venting valve at least to control the flow of air out of the air chamber, a patient valve controlling the patient line, an upper fluid valve, near the top of the air chamber, and a lower valve at least to control the flow of fluid from the air chamber to the set interface.

Further, in accordance with a preferred embodiment of the present invention, in the treatment state the patient and the lower valves are open and the venting and the upper valves are shut. In the priming state, the patient and upper valves are open and the venting and lower valves are shut. In the venting state, the patient and lower valves are closed and the venting and upper valves are open.

Still further, in accordance with a preferred embodiment of the present invention, the manual dial includes an actuator locking mechanism to lock the actuator between states.

Moreover, in accordance with a preferred embodiment of the present invention, the venting valve includes a buoy valve at least to keep fluid from exiting through the vent. The vent can be a swabbable valve connector.

Additionally, in accordance with a preferred embodiment of the present invention, the air chamber includes unit for indicating fluid/air level.

Further, in accordance with a preferred embodiment of the present invention, the air trap module includes a positioning connector to connect the air trap module in a predefined position relative to the pump. For example, the positioning connector can include an identifier to be sensed by the pump.

Moreover, in accordance with a preferred embodiment of the present invention, the line can include a unit to connect the air trap module upstream of the pump.

There is also provided, in accordance with a preferred embodiment of the present invention, a method for an intravenous pump. The method includes during venting of an air trap module, pumping a pre-defined volume downstream of the pump.

Moreover, in accordance with a preferred embodiment of the present invention, the pre-defined volume is a function of the volume of an air trap chamber forming part of the air trap module.

Further, in accordance with a preferred embodiment of the present invention, the method includes receiving input of the volume of a receiving collecting unit and determining when the collecting volume is at least close to filled as a function of multiple pumping cycles of the pre-determined volume.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1A:
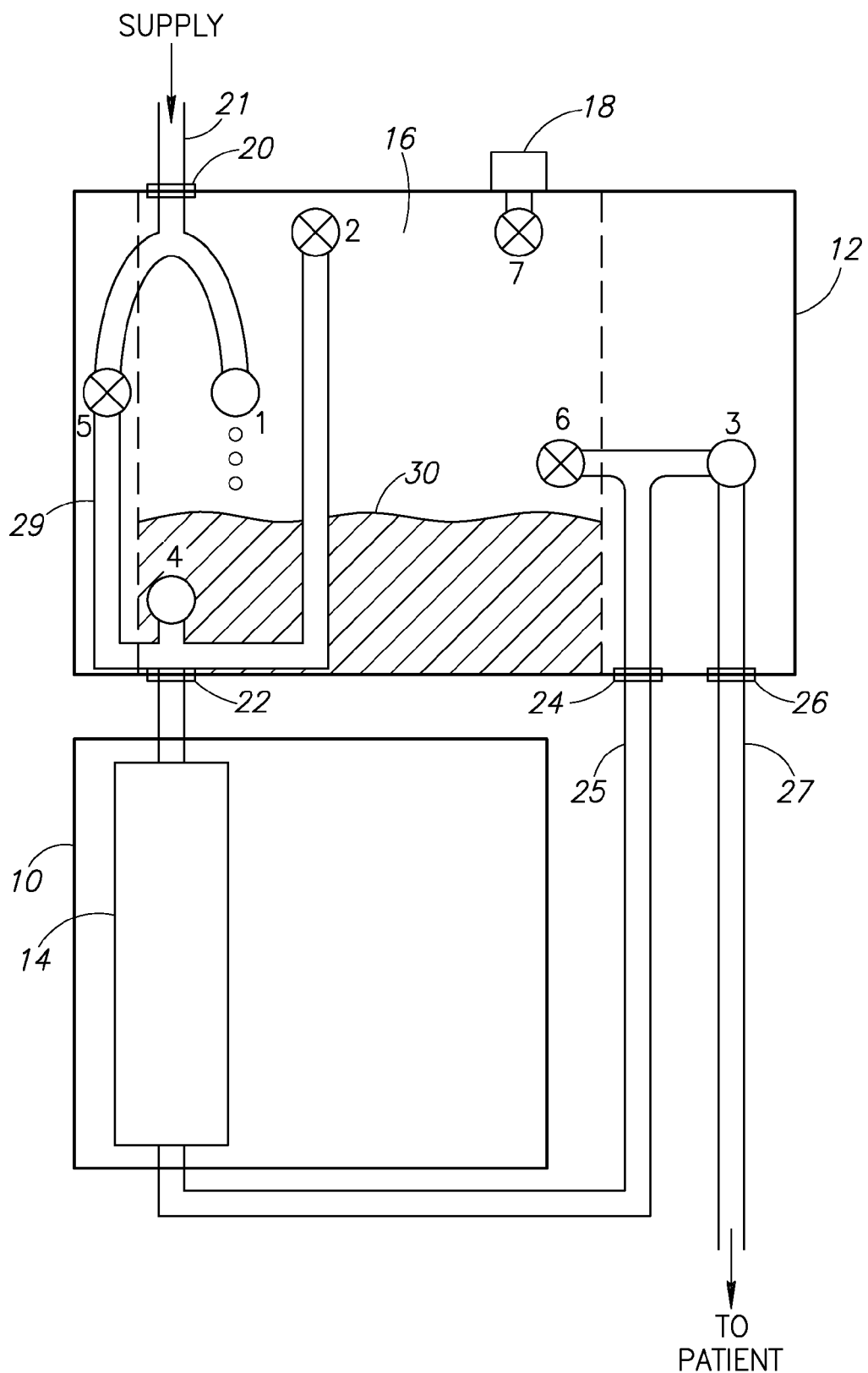
FIGS. 1A, 1B and 1C are schematic illustrations of three operational modes of an infusion pump with a connectable air trap module, constructed and operative in accordance with a preferred embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Applicants have realized that adding a stand-alone air trap chamber, separate from the pump and as part of the tubing connecting the bag to the pump, may enable the air bubbles to be collected in one place, to be safely removed. Moreover, Applicants have realized that the fluid already in the tubes may be utilized to push the air out of the air trap chamber and into a closed container, thereby removing the air without detaching the tubes from the pump or from the patient and without the need to spill fluid to refill the tubes. As a result, there may be little or no contamination of the patient. For expensive drugs like chemotherapy drugs, the lack of spillage represents a significant savings, not to mention the fact that, with little or no spillage, the dosage prescribed is the dosage received.

In one embodiment, which has a bypass path, the bypass fluid may be returned to the air trap chamber to push the air out of the air trap. In another embodiment, the pump may pull the air out of the air trap chamber directly to the vent. In both cases, the air trap is refilled with fresh fluid.

The apparatus described below is particularly relevant for chemotherapy applications, where spillage is of great concern; however, it will be appreciated that the apparatus may be utilized for all types of infusion operations since the apparatus of the present invention may maintain a closed system which may minimize patient contamination. It will also minimize the time needed to remove air from the IV system.

It will be appreciated that, as described in more detail hereinbelow, the air removal and refilling of the fluid are all done by the pump operating in its normal (i.e. forward) mode of operation and without stopping all the pump standard alerts. This further enhances the safety of the patient while removing the air from the system.

Figure 1B:
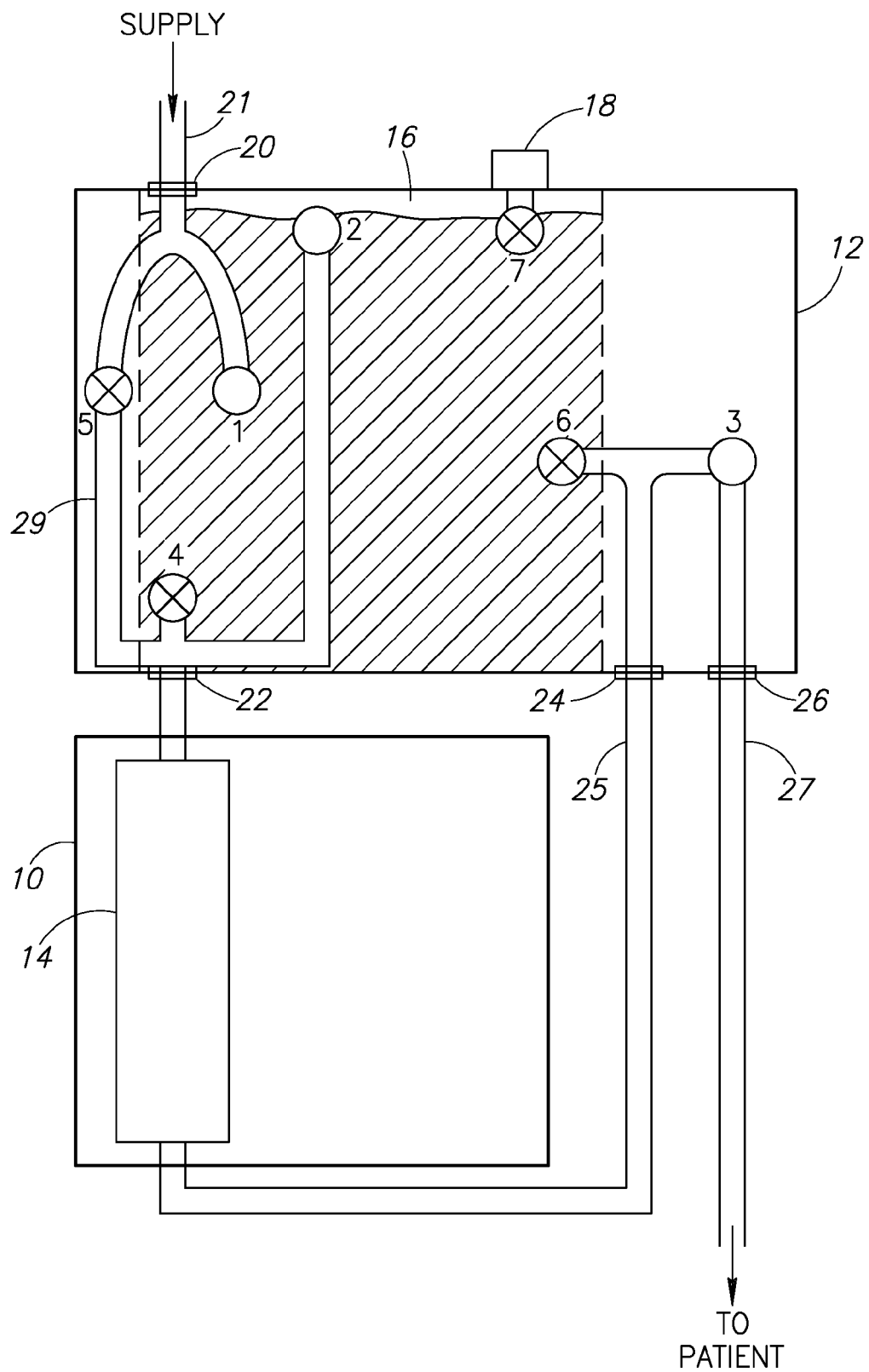
Figure 1C:
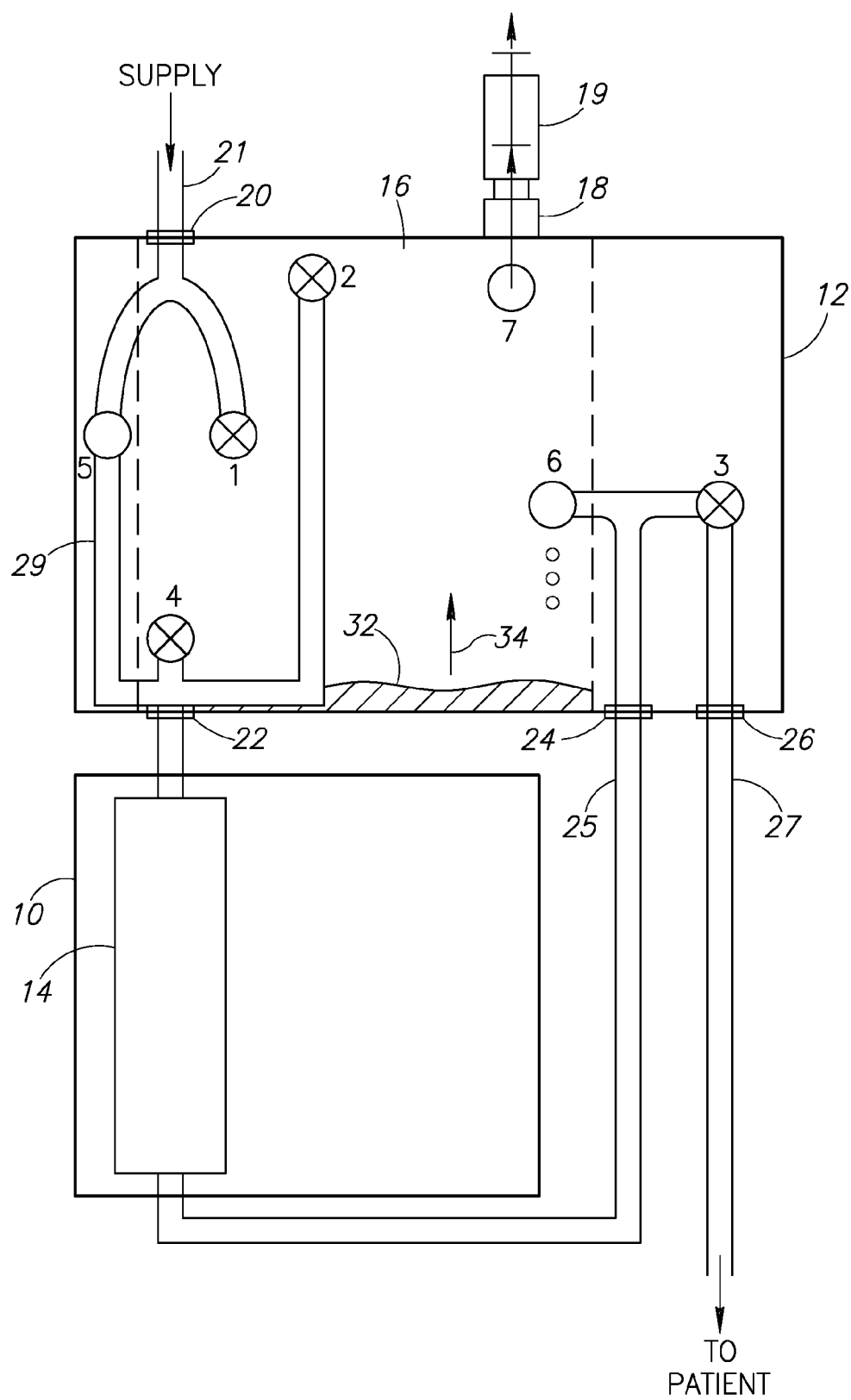
Figure 1D:
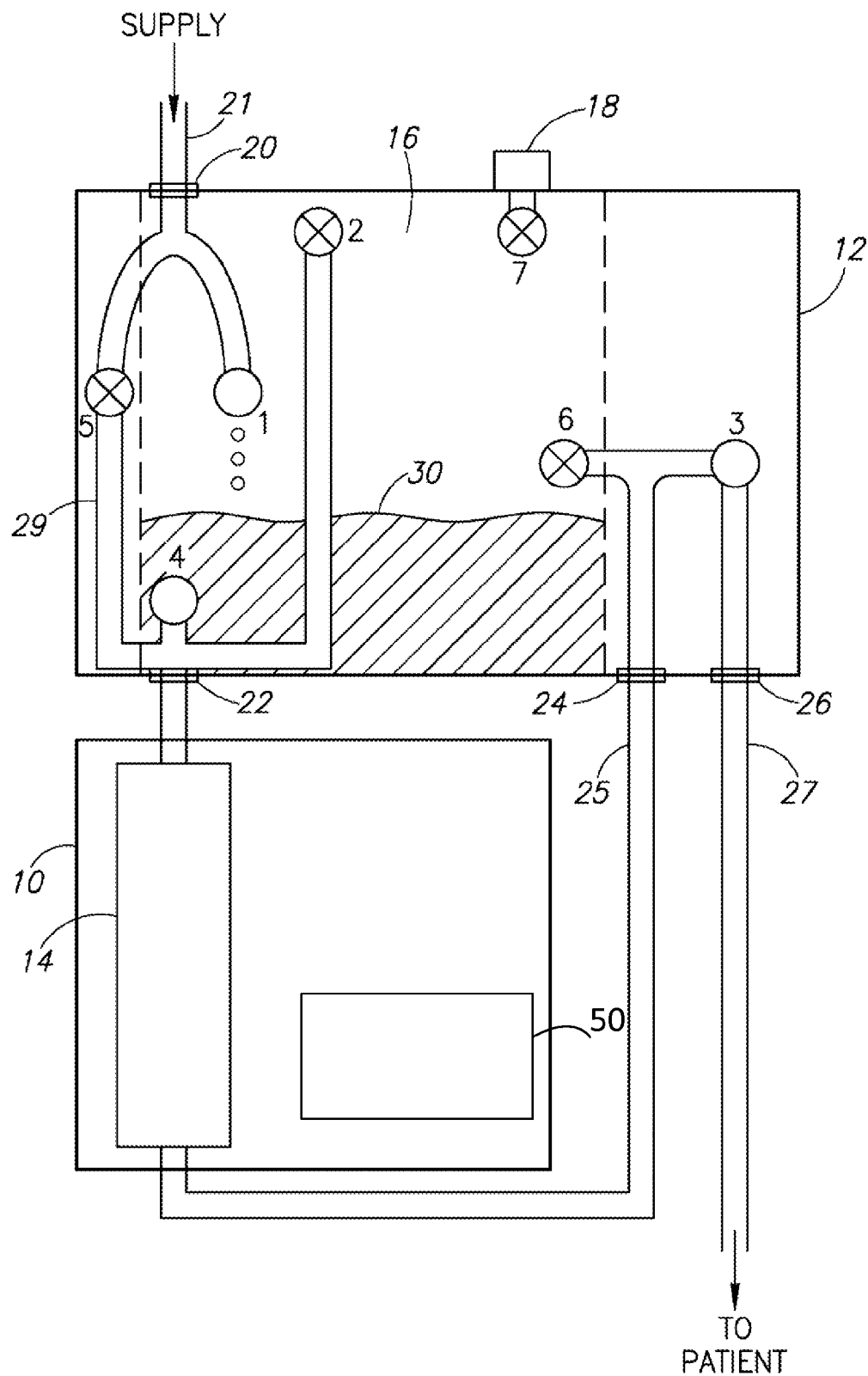
FIG. 1D is a schematic illustration of an operational mode of an infusion pump with a connectable air trap module, constructed and operative in accordance with an embodiment of the present invention.

Reference is now made to FIGS. 1A, 1B and 1C, which illustrate three alternate operational modes of an infusion pump 10 with a connectable air trap module 12, connected to the tubes providing fluids, such as chemotherapy fluids, to the patient. Pump 10 may operate on a "set interface" 14, which may be a portion of the tubes capable of receiving the pumping action. Pump 10 may also provide an air bubble detector (not shown) to stop the pump action if an air bubble is detected in set interface 14. As described herein below, the air trap chamber may be combined with the set interface as one physical unit Reference is further made to FIG. 1D, which is substantially similar to FIG. 1A further including air bubble detector 50.

Figure 2A:
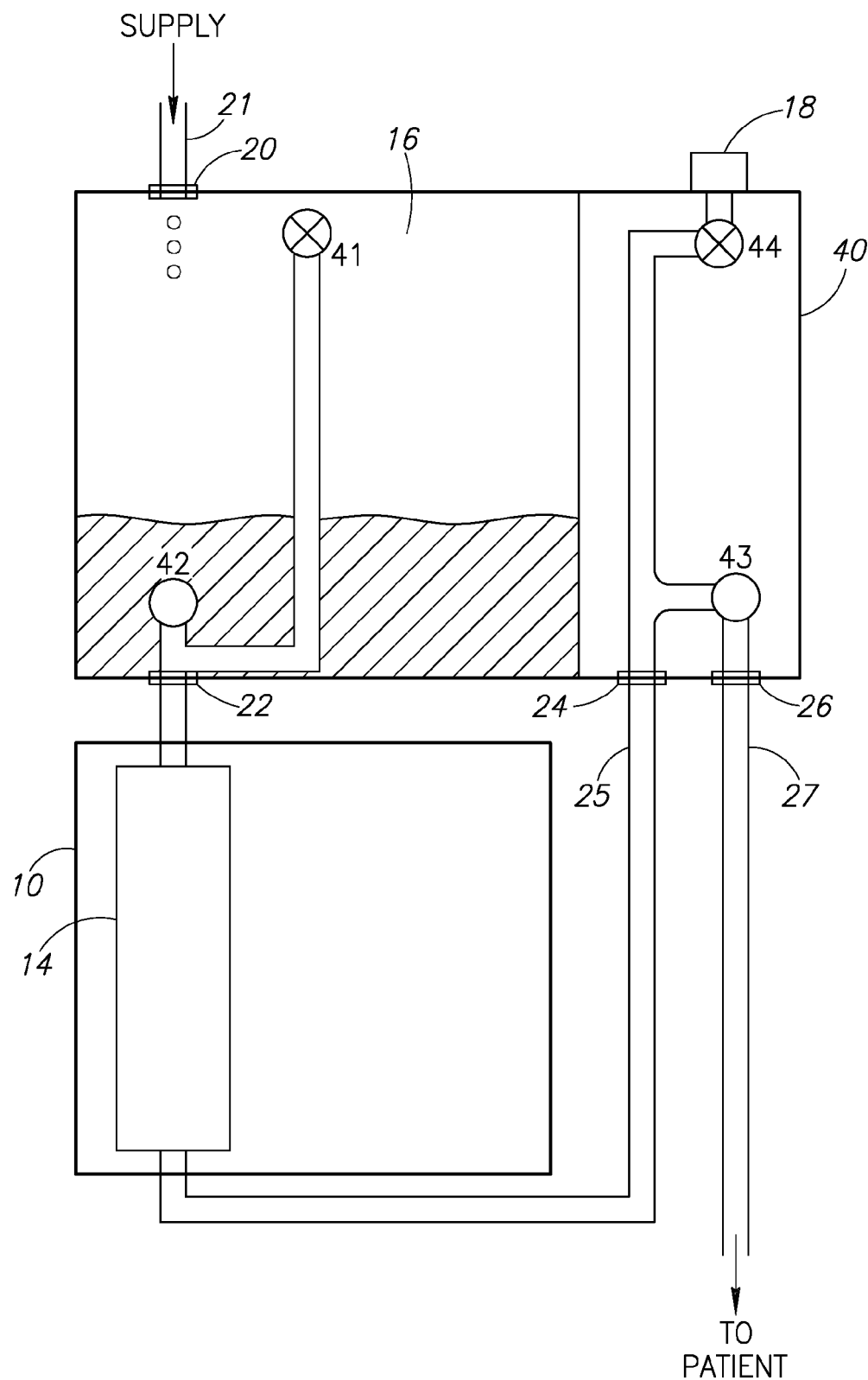
FIGS. 2A, 2B and 2C are schematic illustrations of three operational modes of an infusion pump with an alternative connectable air trap module, constructed and operative in accordance with an alternative, preferred embodiment of the present invention.
Figure 2B:
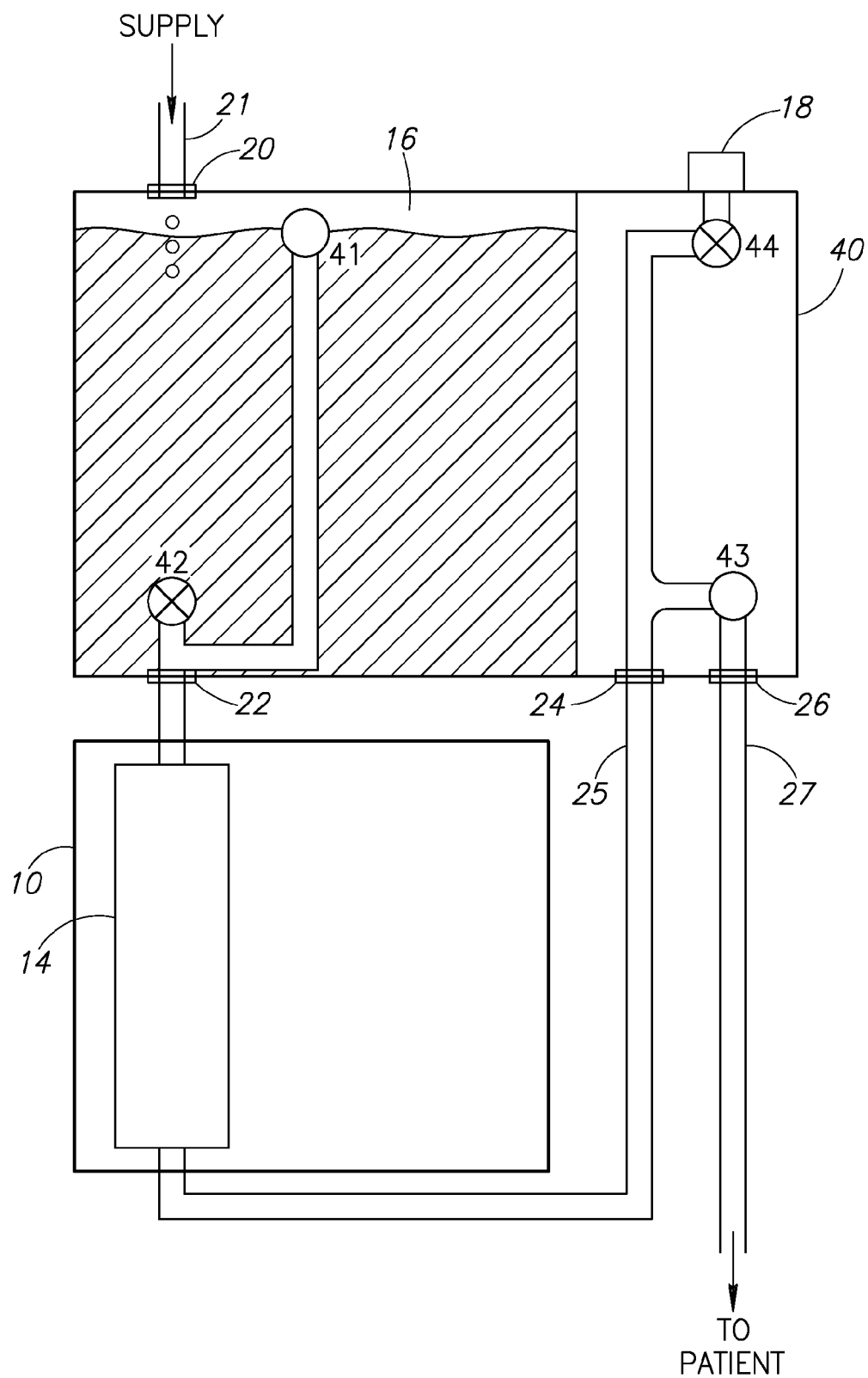
Figure 2C:
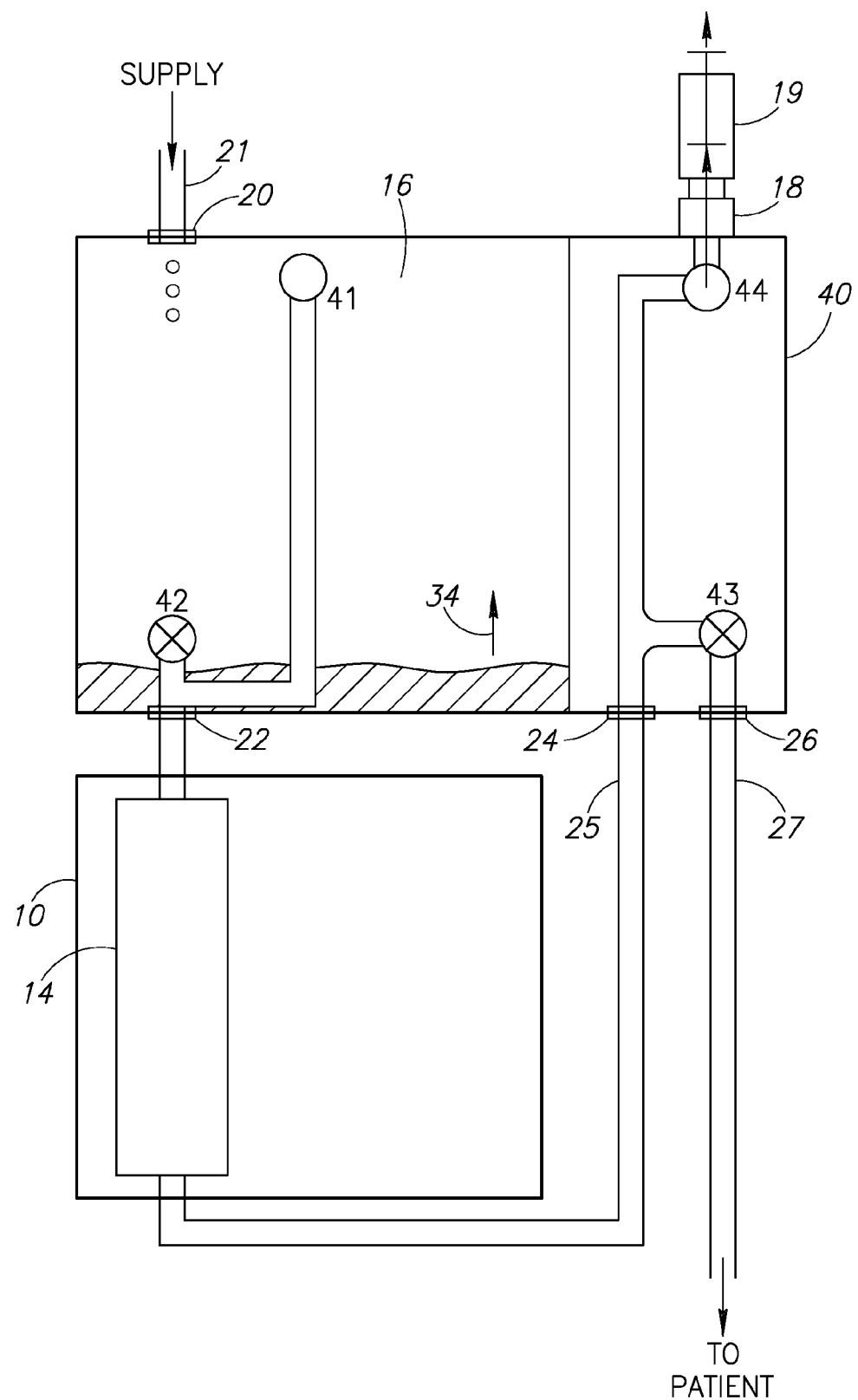

Air trap module 12 may be connected to set interface 14, prior to pump 10 and above it, thereby to receive air flowing in the supply line 21. Air trap module 12 may have an air trap chamber 16 and a vent 18 therein, as well as a plurality of valves to control the flow of fluid into and out of air trap chamber 16 and to control the flow of air out of air trap chamber 16. In the embodiment of FIGS. 1A, 1B and 1C, there are 7 valves, labeled 1-7. In the embodiment of FIGS. 2A, 2B and 2C, described hereinbelow, there are 4 valves.

In accordance with a preferred embodiment of the present invention, air trap module 12 may also have four line connections, a supply connection 20 to a supply line 21, a set interface connection 22 to tubing connected to set interface 14, a return connection 24 connectable to a return line 25 connected after set interface 14 and a patient connection 26 connectable to a patient line 27 connectable to the patient.

Air trap module 12 of FIG. 1 may have 7 valves (indicated by circles), to control the fluid and air flow through the various lines. The 7 valves may be a supply line valve 1 controlling supply line 21 into air trap chamber 16, an upper valve 2 controlling fluid (or accumulated fumes) flowing from the top of air trap chamber 16, a patient valve 3 controlling fluid flow from return line 25 into patient line 27, a lower valve 4 controlling fluid flow into set interface 14, a bypass valve 5 controlling flow from supply line 21 into an internal bypass line 29, a return valve 6 controlling flow from return line 25 back into air trap chamber 16 and a venting valve 7 venting air out of air trap chamber 16.

In general, there may be 3 operational modes, a treatment mode shown in FIG. 1A, during which the fluid (chemotherapy or otherwise) may be provided to the patient, a priming mode shown in FIG. 1B, during which the various tubes may be filled completely with fluid, and a venting mode shown in FIG. 1C, during which toxic air, in the chemotherapy case, trapped in air trap chamber 16 may be pushed out of vent 18 and into any suitably closed unit, such as a syringe 19 (shown), an empty bag, etc., thereby to keep the toxic air from affecting any of the staff.

It will be appreciated that vent 18 and its associated venting valve 7 may be located generally at the top of air trap chamber 16, thereby to allow the air to rise and to be pulled out without squeezing air trap chamber 16.

In a further pre-operation mode (not shown in the figures), all valves 1-7 may be open, thereby connecting all internal passages. This may allow free flow of sterilization gases throughout module 16, a typical requirement for an ETO type of sterilization. Typically, this mode may be active only during manufacturing or by a specially trained technician and may no longer be accessible once regular operation begins.

Referring now to FIG. 1A, during the treatment mode, fluid may flow from the supply line, through pump 10, to the patient. Thus, in this mode, supply valve 1 is open (indicated by an open circle) for fluid to flow from supply line 21 into air trap chamber 16 and lower valve 4 is open for fluid to flow out of air trap chamber 16 and into set interface 14. During this mode, air bubbles flowing with the fluid may break away from the flow and may rise into air trap chamber 16 where they will start to accumulate. Patient valve 3 is open for fluid to flow from return line 25 into patient line 27. However, the remaining valves are closed (indicated by an X in the circle) to keep fluid from flowing to the wrong places. It will be appreciated that air trap chamber 16 may have some fluid in it, as indicated by a fluid line 30. Typically in this mode at least part of the air trap module is filled with fluid.

Referring now to FIG. 1B, during the priming mode, fluid may flow to fill up the lines, before the lines are attached to the patient. No air may be allowed to be in the system. Thus, air trap chamber 16 may be filled fully with fluid such that the fluid will flow out of upper valve 2 directly to set interface 14. In addition, supply valve 1 is open for fluid to flow into air trap chamber 16 and patient valve 3 is also open for fluid to flow from return line 25 into patient line 27. The remaining valves are closed. Fluid may be allowed to flow to the end of patient line 27, in order to prime the system.

As mentioned hereinabove, during treatment, the chemotherapy fluid may generate gases which form air bubbles in the flow, typically as the fluid flows from supply line 21. Air trap chamber 16 may trap these gases and may fill up. Thus, FIG. 1C shows a fluid line 32 in the lower portion of air trap chamber 16. It is also possible that air trap chamber 16 may be filled entirely with air. After air trap chamber 16 may be full with air, air bubbles may start to flow through valve 4 until they enter set interface 14, where they may be detected by the air bubble detector forming part of pump 10. The air bubble detector may shut off the action of pump 10 and may activate an alarm which may not stop until a member of the medical staff may come to shut it off. The staff member may then switch air trap module 12 to the venting mode, to remove the air from air trap chamber 16 and from set interface 14, as follows:

In the venting mode, in accordance with a preferred embodiment of the present invention, the input to pump 10 may be switched to come directly from supply line 21, via bypass line 29, thereby to ensure that fluid may be pushed through return line 25 back into air trap chamber 16, to push the air out through vent 18. To enable this, bypass valve 5, return valve 6 and vent valve 7 are opened. Bypass valve 5 may provide fluid directly from supply line 21 through set interface 14 to return line 25 and return valve 6 may allow the fluid from return line 25 to flow back into air trap chamber 16, thereby filling air trap chamber 16 with fluid (indicated by arrow 34) which, in turn, may push the toxic air through valve 7 and out vent 18, preferably into a closed unit, such as syringe 19.

The remaining valves, supply valve 1, lower valve 4, upper valve 2 and patient valve 3, are all closed, to keep the air from the patient. Thus, with pump 10 pushing fluid, via return line 25, back into air trap chamber 16, the present invention may flush undesired air out of air trap chamber 16, without disengaging patient line 27 from the patient and without exposing staff members to any of the noxious air.

As mentioned hereinabove, during manufacture of any medical device, all passages of the device must be sterilized. For ETO sterilization, sterilization gases are passed through the device. In the present invention, when all the valves are open, the sterilization gases may pass from one section of the chamber to the next and thus, the device may be sterilized.

Figure 2D:
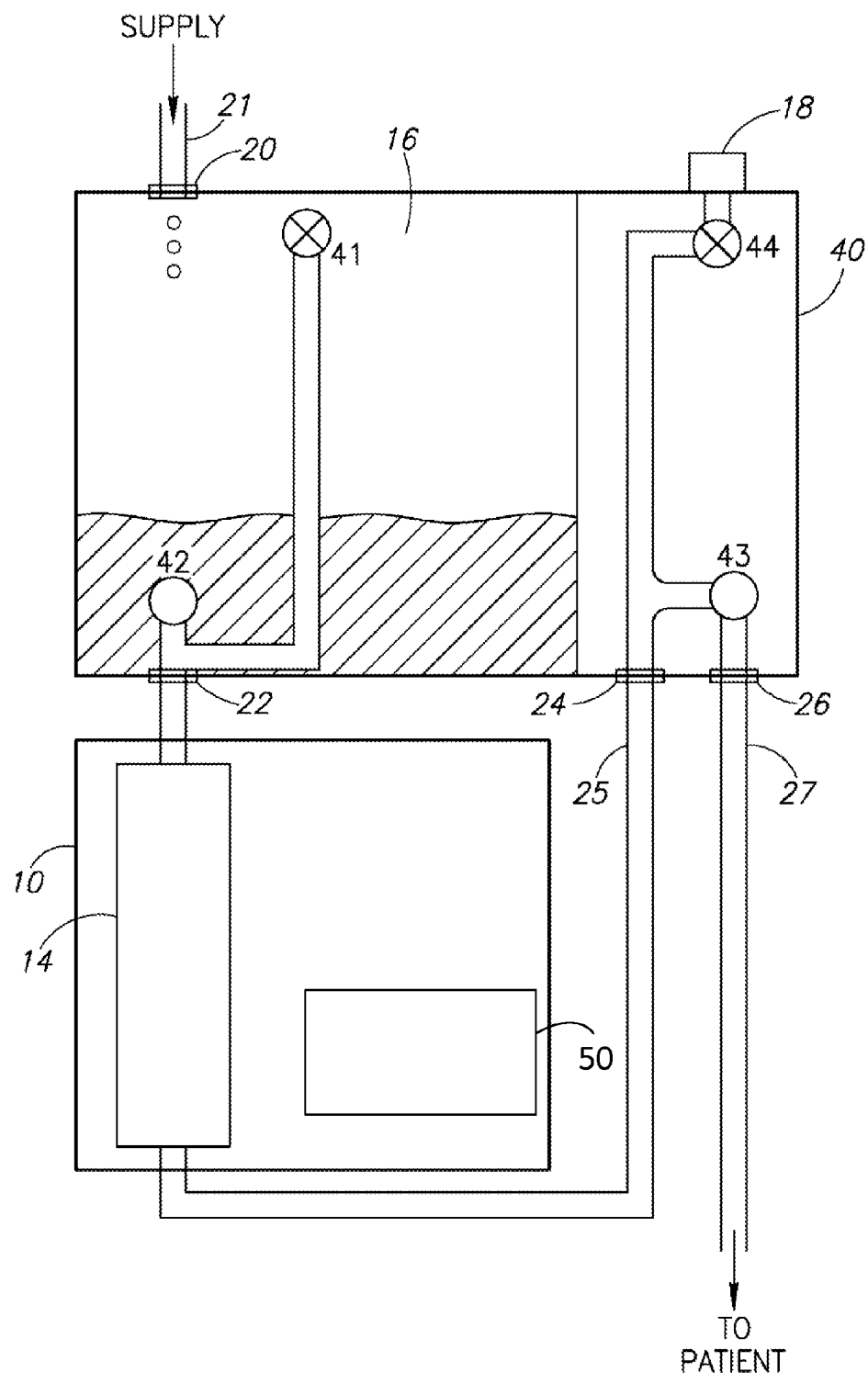
FIG. 2D is a schematic illustration of an operational mode of an infusion pump with a connectable air trap module, constructed and operative in accordance with an embodiment of the present invention

Reference is now made to FIGS. 2A, 2B and 2C, which illustrate the same three modes as FIGS. 1A, 1B and 1C but for a four valve air trap module 40. Similar items carry similar reference numerals. As in the previous embodiment, there is an air trap chamber 16 and there are four line connections 20, 22, 24 and 26, connected as in the previous embodiment to line 21, set interface 14, return line 25 and patient line 27, respectively. Reference is further made to FIG. 2D, which is substantially similar to FIG. 2A further including air bubble detector 50.

However, in this embodiment, there may be four valves 41-44 to air trap module 40, two controlling flow through air trap chamber 16 and two controlling the output flow, either to patient line 27 or to vent 18. The two controlling flow through air trap chamber 16 may be an upper valve 41 controlling fluid and air flowing from the top of air trap chamber 16 and a lower valve 42 controlling fluid flow from air trap chamber 16 into set interface 14. The two controlling the output may be a patient valve 43 controlling fluid flow into the patient, and a venting valve 44 venting undesired air out of air trap module 40.

Referring now to FIG. 2A, during the treatment mode, fluid may flow directly from supply line 21 into air trap module 40, being pulled into air trap module 40 by the operation of pump 10. Lower valve 42 is open for fluid to flow out of air trap module 40 and into set interface 14. Patient valve 43 is also open, for fluid to flow out of air trap module 40 and into patient line 27. However, the remaining valves are closed.

Referring now to FIG. 2B, during the priming mode, fluid may flow to fill air trap module 40 such that the fluid may flow out of upper valve 41 directly to set interface 14, through return line 25, and into patient line 27 via patient valve 43. As in the previous embodiment, fluid may be allowed to flow to the end of patient line 27, in order to prime the system.

In the venting mode, with air trap module 40 full of air, the air may be pumped by pump 10 out of upper valve 41, through return line 25 and out through vent 18. Thus, lower valve 42 and patient valve 43 are closed, to keep air from the patient, and upper valve 41 and vent valve 44 are opened. As the air is being removed, fluid will begin to flow from supply line 21, filling air trap chamber 16 and return line 25, such that, once all of the air is removed, the system may return to the treatment mode.

It will be appreciated that, in this embodiment, the air detector of pump 10 may be shut off during removal of the air, so as not to detect the air flowing past the pump during the removal process.

Venting valve 7 or 44 may be any suitable venting valve. For example, it may have a buoy to prevent the flow fluid out vent 18 once all of the air has been removed. If the buoy is a one directional buoy, the buoy may rise up the valve as the fluids rise in air chamber 16 and may block the opening of valve 7 or 44 as a result. This may keep fluids from being vented into the collection bag or syringe 19. If the buoy is a two directional buoy, it may also prevent the return of existed fluids collected in a collection bag back to the air trap chamber system. Vent 18 may have a check valve, typically a swabbable valve connector, which may prevent accidental air discharge.

It will be appreciated that, in both embodiments, air trap chamber 16 has two valves, lower valve 4 or 42 and upper valve 2 or 41 to control the flow of fluid and/or air, depending on the operational mode. It will be appreciated that this enables air trap module 12 or 40 to handle both the presence of fluid and the presence of air without having to disconnect the patient from patient line 27.

It will further be appreciated that air trap chamber 16 may provide a buffer for collecting air. Its size may define the amount of air to be collected which, in turn, may define the amount of time the medical staff has between air removals. It is possible that, with the existence of this buffer per patient, the medical staff may be able to clear the various air trap chambers of a treatment room of patients before the various air trap chambers 16 fill up completely.

It will further be appreciated that air trap modules 12 and 40 may be connected to any suitable type of pump. For each of the operational modes, pump 10 merely pumps in a forward direction; where the fluid or air goes is controlled by valves 1-7 or 41-44.

It will further be appreciated that, for air trap module 12, air may reach the air detector of pump 10 which may cause pump 10 to stop operating. However, since, during the venting operation, the substance flowing through the pump is fluid from the bypass path, the air detector of pump 10 may remain operative during venting of the air.

It will further be appreciated that valves 1-7 or 41-44 may be implemented mechanically or electro-mechanically. In the mechanical configuration, there may preferably be a single actuator controlling all valves states. In the electro-mechanical case, each valve may be separately programmed or they may be programmed to open or close as a group. In this embodiment, there may be an external actuator connected to pump 10.

Figure 3A:
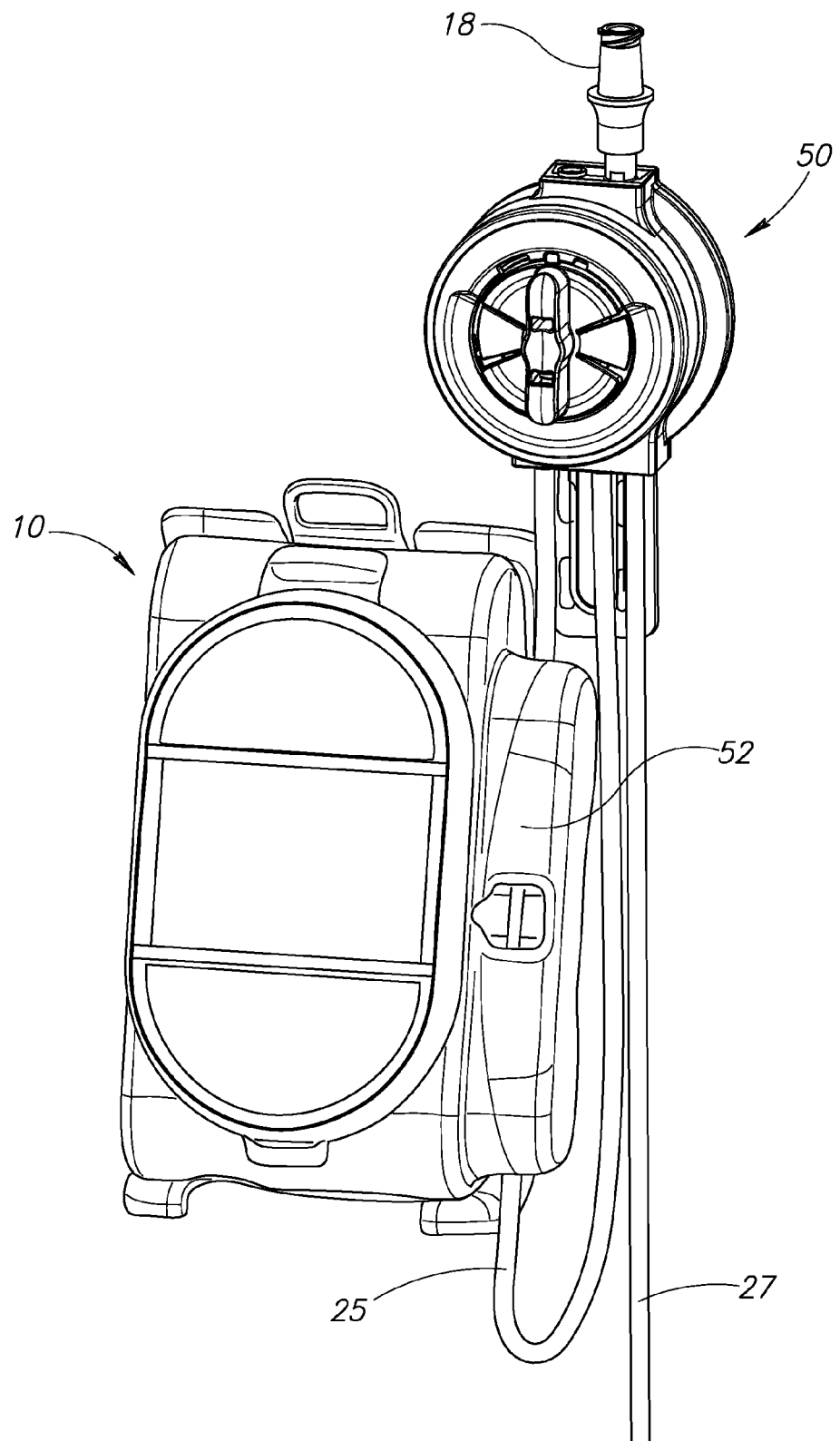
FIGS. 3A and 3B are isometric illustrations of an exemplary embodiment of air trap module of FIG. 1 connected to a pump.
Figure 3B:
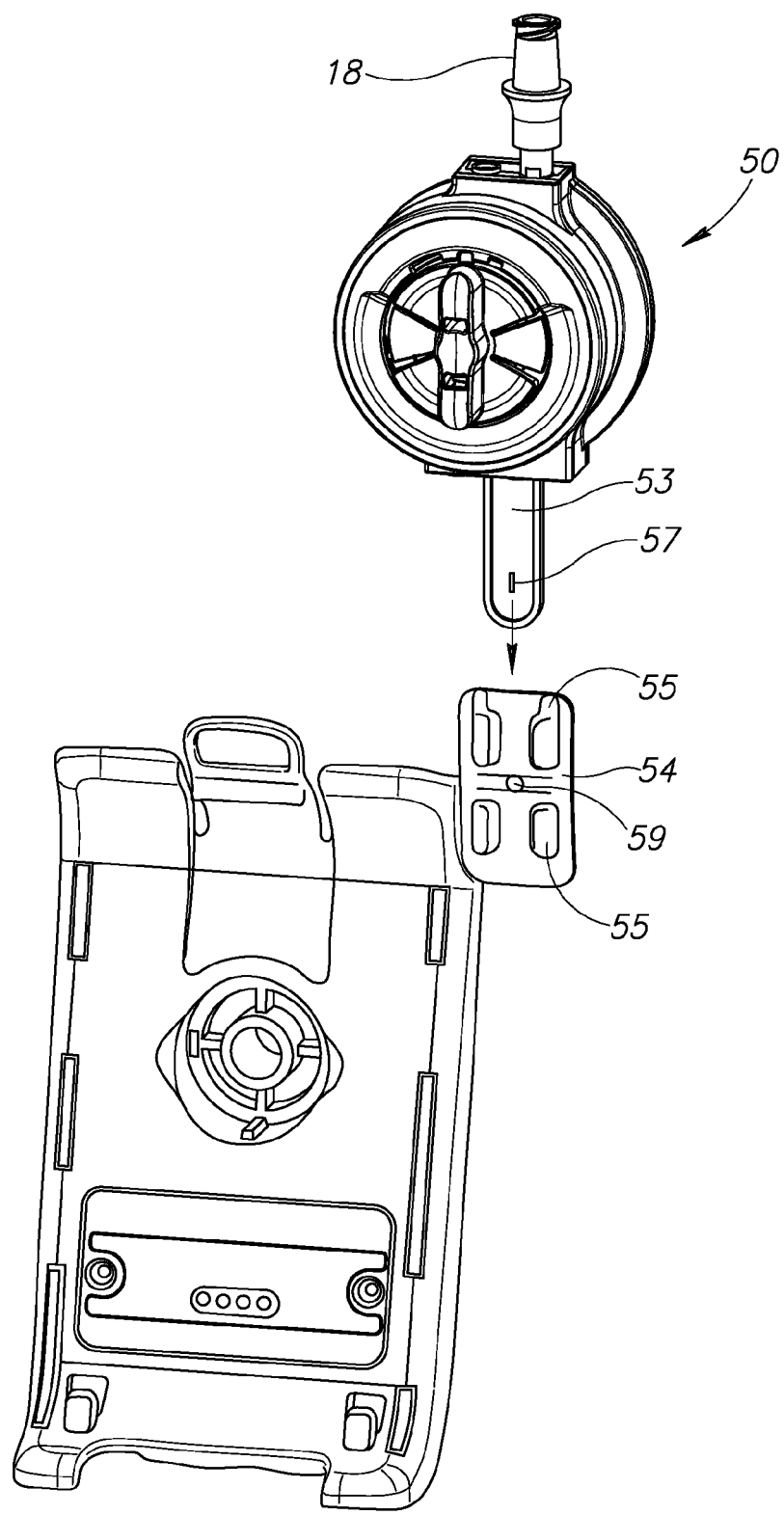

Reference is now made to FIGS. 3A and 3B which illustrate an exemplary embodiment of the seven valve air trap module, implemented as a round unit with mechanically controlled valves. FIG. 3A illustrates the air trap module 50 connected to the pump and FIG. 3B details how the connection to pump 10 is implemented. Thus, FIG. 3A shows air trap module 50, with vent 18, connected to pump 10 with return line 25 and patient line 27. FIG. 3A also shows a housing 52 for set interface 14. FIG. 3B shows a holder 54 forming part of a pump cradle used to hold pump 10 to an IV pole. Holder 54 may include flanges 55 to hold a stick-like portion 53 of air trap module 50 in place.

Optionally, stick 58 may include an identification element 57, such as a small magnet, therein and holder 54 may include an identifying sensor 59, such as a Hall effect sensor. Sensor 59 may sense the presence or absence of identification element 57 and may provide its output to pump 10. Element 57 and sensor 59 may enable automatic set recognition when air trap module 12 or 40 may be attached on to the pump.

It will be appreciated that stick 53 may allow the air trap module to be maintained in its correct position, upstream of the pump, allowing proper air accumulation in air chamber 16. Thus, when the AT chamber is full with air and bubbles are starting to flow into the pump, the internal air bubble sensor of pump 10 may detect the bubbles and may stop pumping fluid, thereby protecting the patient. Stick 53 is only one embodiment; other fastening elements may maintain proper air accumulation as well FIGS. 4A and 4B, to which reference is now made, detail air trap module 50 with a dial knob 56 in front and an approximately oval shaped volume 58 functioning as air trap chamber 16 in the back. Volume 58 may be of any size; for example, it may hold 2-4 ml. Module 50 may also include fluid gauge minimum and maximum level indicators 60 and 62, to provide an indication of the level of fluid in volume 58. Volume 58 may be formed of a clear plastic such that a user can see the air/fluid level at any time; thus, indicators 60 and 62 may simply mark the lowest and highest volume levels. In an alternative embodiment, module 50 may be connected to a fluid level meter to better determine the air level in chamber 16. For example, the meter may be a floating ball. In a still further embodiment, the air trap chamber may have an integrated electrical level meter which may trigger alarms and/or may trigger the start or stop of various modes.

Figure 4A:
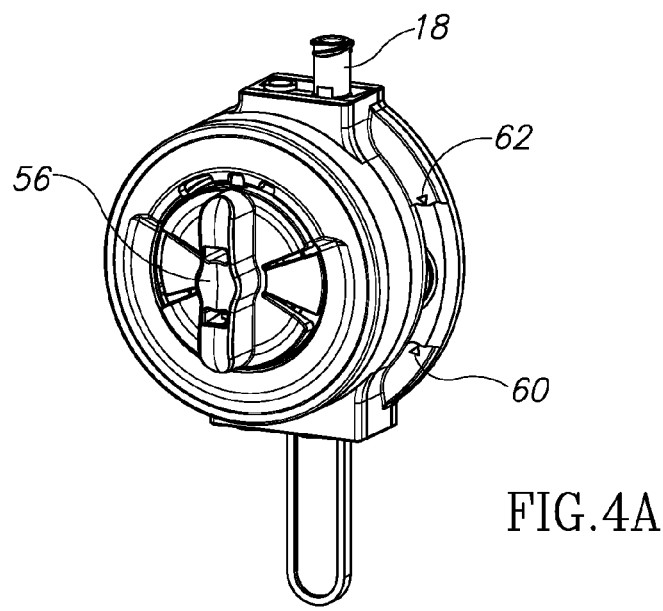
FIGS. 4A and 4B are isometric illustrations of the air trap module of FIG. 3 with a dial knob actuator in the front and an air trap chamber in the back.
Figure 4B:
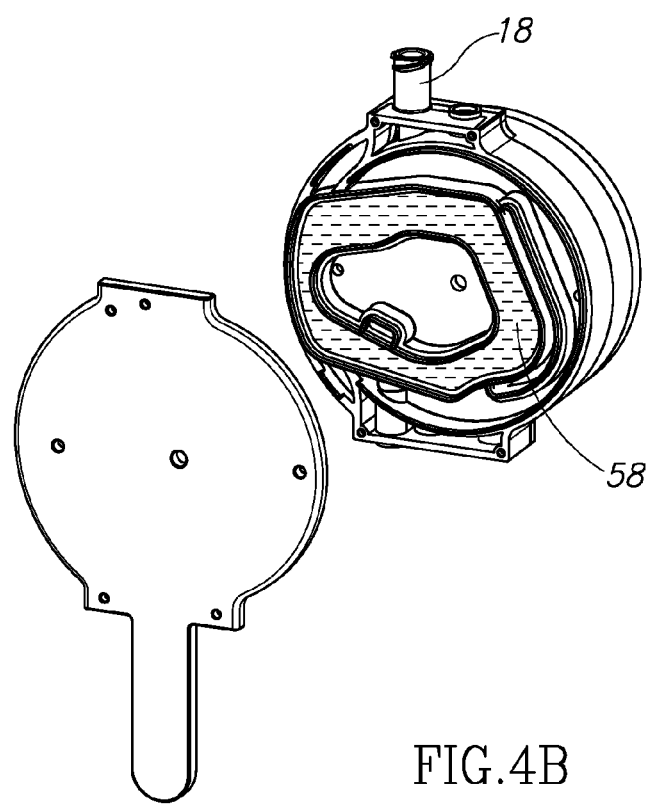

The knob in FIG. 4A may be rotated only after the user pushes it slightly inwards. After releasing the knob, it will spring back to lock itself safely in one of the operating modes.

Dial knob 56 may have multiple positions, each controlling a different mode of operation. Four positions are shown, for infusion, venting, priming and an optional sterilization mode (labeled ETO). As will be described in more detail hereinbelow, as knob 56 moves from one position to another, the valves open and close to come to the states discussed hereinabove. It will be appreciated that knob 56 is a single handle which provides all modes. This may provide a simple and relatively reliable operation.

Figure 5:
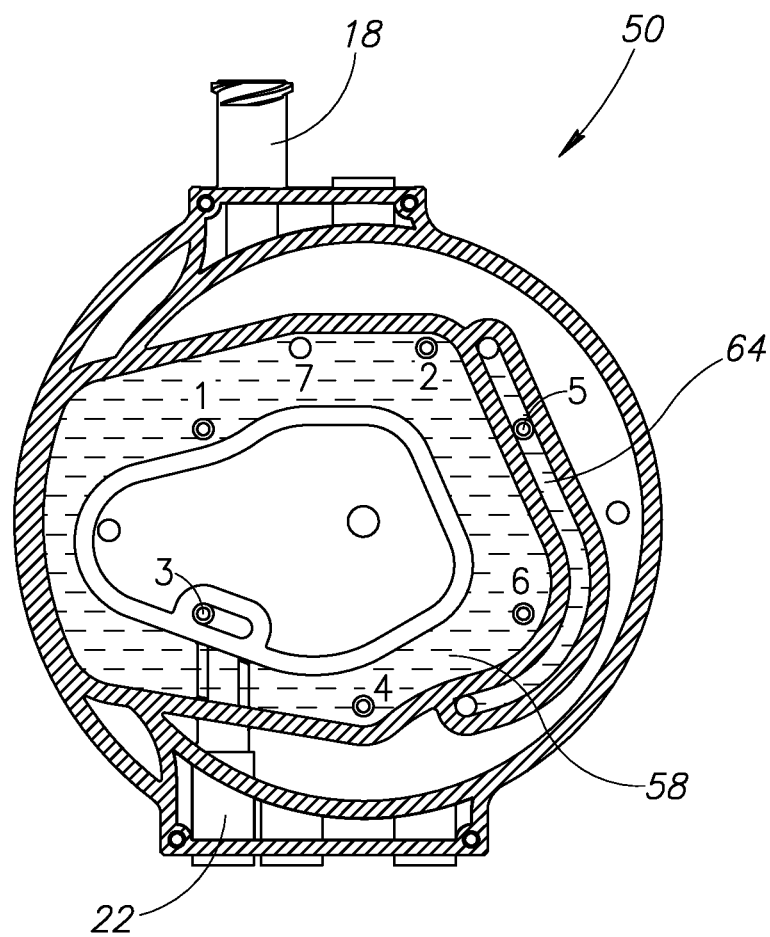
FIG. 5 is a back view illustration of the air chamber of FIG. 4B indicating the locations of the various valves in air trap module.

FIG. 5, to which reference is now briefly made, indicates the locations of the various valves 1-7 in air trap module 50. Note that venting valve 7 is near vent 18, bypass valve 5 is above a bypass path 64 and patient valve 3 is above connection 26 to patient line 27.

Figure 6A:
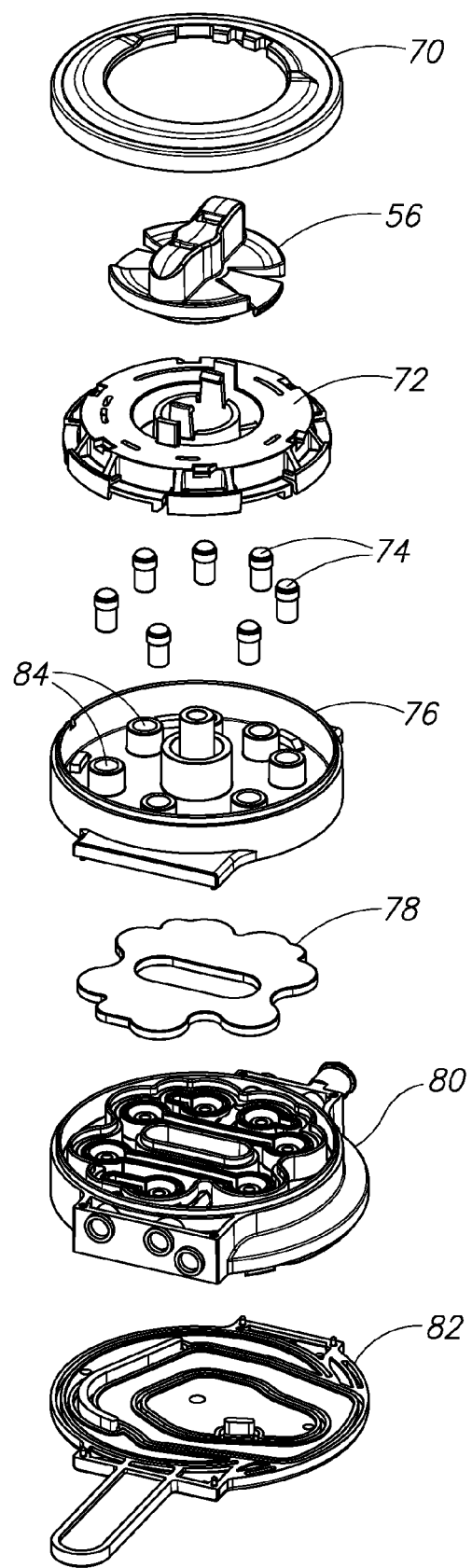
FIG. 6A is an exploded view of the elements of the air trap module of FIG. 3.
Figure 6B:
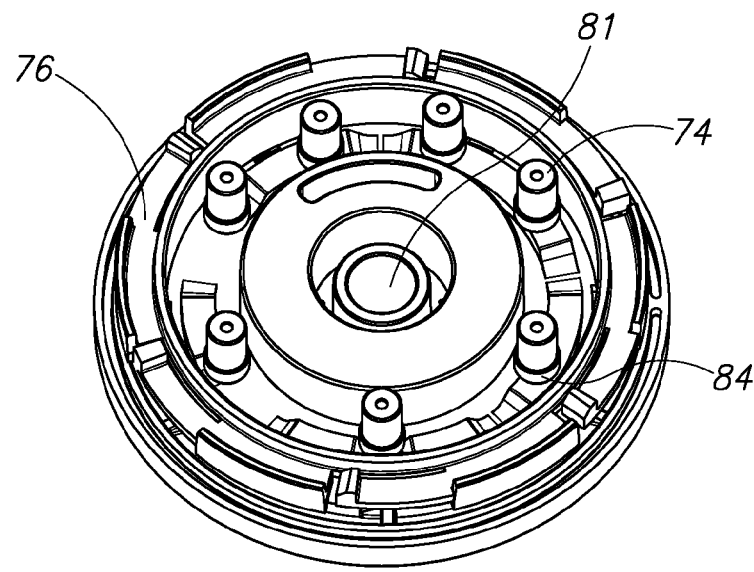
FIG. 6B is an isometric illustration of the some of the inner elements of FIG. 6A combined together.
Figure 6C:
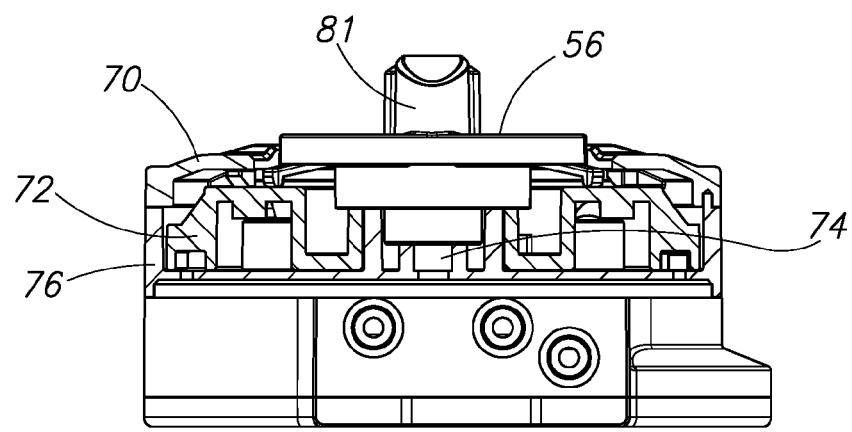
FIG. 6C is a sectional view of the module of FIG. 6A (not exploded)

FIGS. 6A, 6B and 6C, to which reference is now briefly made, detail air trap module 50, where FIG. 6A provides the elements of air trap module 50 in exploded view, FIG. 6B illustrates the inner elements combined and FIG. 6C is a sectional view of the module.

Module 50 may comprise a top cover 70, dial knob 56, a dial 72, seven valve spools 74, a hive 76 of holes, a flexible seal membrane 78, a main body 80 and a bottom cover 82. Note that volume 58 is formed when bottom cover 82 is connected to body 80.

FIG. 6B shows valve spools 74 positioned above dial 72. Note the central cylinder, labeled 81, within which dial knob 56 rotates. It will be appreciated that each valve spool 74 may move up and down within an associated hole 84 of hive 76 and may press against seal membrane 78 to open and close its associated valve. Dial 72 may be designed, as described hereinbelow, to press the appropriate set of valve spools 74 for each mode.

It will be appreciated that other configurations of valves are possible and are incorporated within the present invention.

Figure 7A:
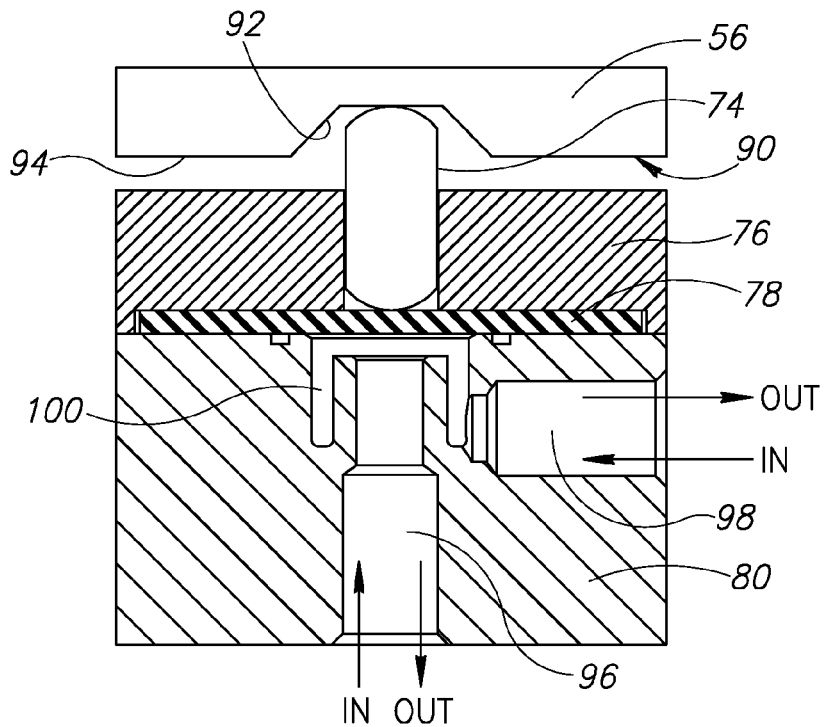
FIGS. 7A and 7B are schematic cross sectional illustrations of a typical valve in the air trap module of FIG. 3, detailing the disengagement (open) and engagement (close) of a typical valve spool, respectively.
Figure 7B:
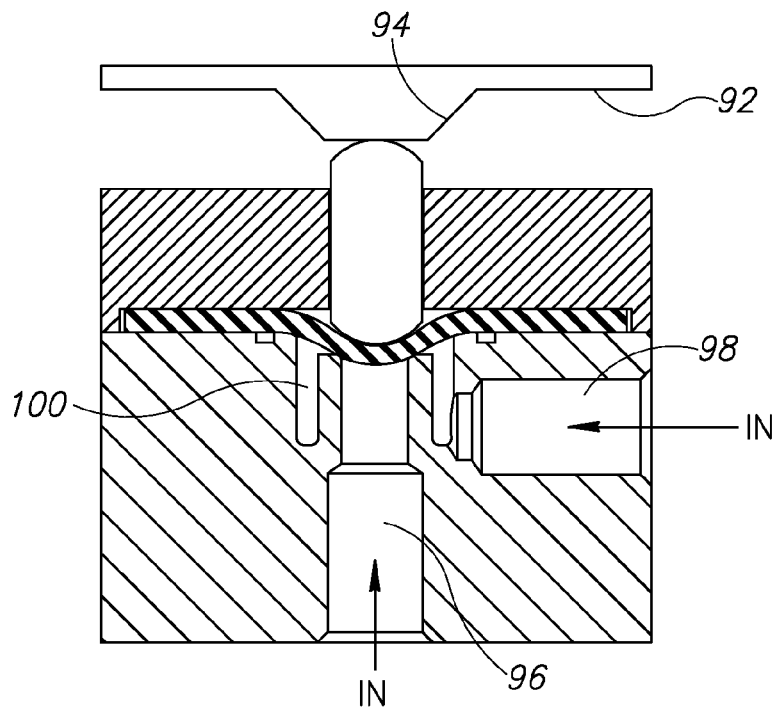

FIGS. 7A and 7B together illustrate a schematic cross section of a typical valve in air trap module 50, detailing the disengagement and engagement of a typical valve spool 74.

Spool 74 may be held in place by one of holes 84 in hive 76 and may be held against flexible seal membrane 78. Dial 72 may comprise an undulating underside 90 which may have recesses 92 and protrusions 94, where protrusions 94 may press each spool 74 down into seal membrane 78 while recesses 92 may allow each spool 74 to rise, typically pushed back by seal membrane 78. The arrangement of the recesses 92 and protrusions 94 may determine which valves open and which close for each of the operational modes.

In accordance with one embodiment of the present invention, there may be a concentric valve configuration comprising a first conduit 96, optionally vertical, in the center of the valve module and a second conduit 98, optionally horizontal, connected together via a circular ditch-like groove 100. The top circular lips of conduit 96 and groove 100 may be located underneath membrane 78.

In FIG. 7A, recess 92 may be above spool 74 and thus, spool 74 may not press against seal 78. As a result, groove 100 may be open and the two conduits 96 and 98 may be connected and fluid and/or air may flow therebetween. In FIG. 7B, protrusion 94 may engage spool 74, thereby pushing it into seal membrane 78 which may then push against groove 100, disconnecting the two conduits 96 and 98 and stopping the flow of fluid and/or air.

Figure 8:
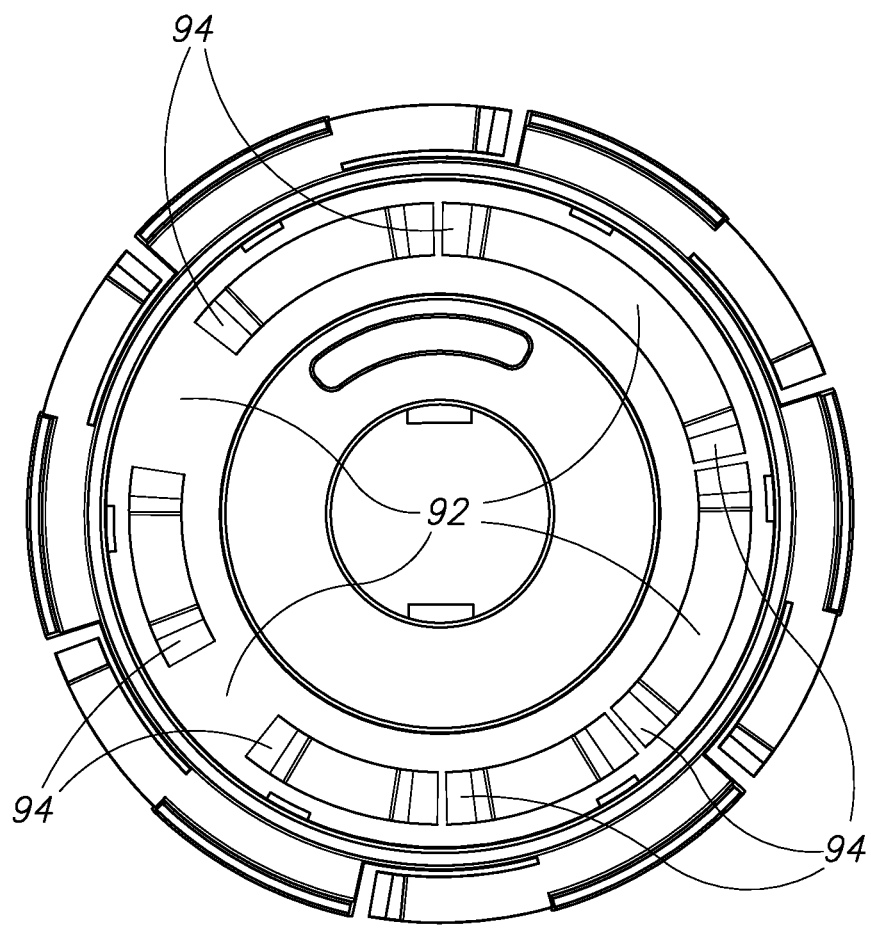
FIG. 8 is an isometric illustration of an undulating underside of a dial of the air trap module of FIG. 3.

FIG. 8, to which reference is now briefly made, illustrates undulating underside 90 of dial 72. Underside 90 may have a plurality of recesses 92 and protrusions 94, not evenly spaced around dial 72. The distance between neighboring protrusions 94 may be a function of which valves 1-7 are open or closed for which mode.

It will further be appreciated that the location of protrusions 94 with respect to each other may enable the present invention to provide a double action safety feature, such as a make before break feature, for changing from one mode to another. Thus, recesses 92 may be located such that, when turning from one mode to another, certain released spools 74 may be closed by their respective protrusions 94 before other spools 74 may be opened by their respective recesses 92. This may enable one mode disengage completely before the next mode engages, which may be useful for the venting mode which may cause a buildup of pressure in air trap module 16. This pressure may be released when returning from venting mode back to treatment mode by ensuring that closed supply valve 1 will open (to release pressure back into supply line 21 instead of into the patient) before open return valve 6 is closed and closed patient valve 3 is opened.

FIGS. 9A, 9B, 9C and 9D illustrate the fluid flow for each of the treatment, priming, venting and sterilization states, respectively, for air trap module 50. During treatment, fluid flows from a fluid bag 110 to supply valve 1, through chamber 58 to lower valve 4 through set interface 14 (operated on by pump 10) and return line 25 and from return line 25 to patient valve 3.

Figure 9C:
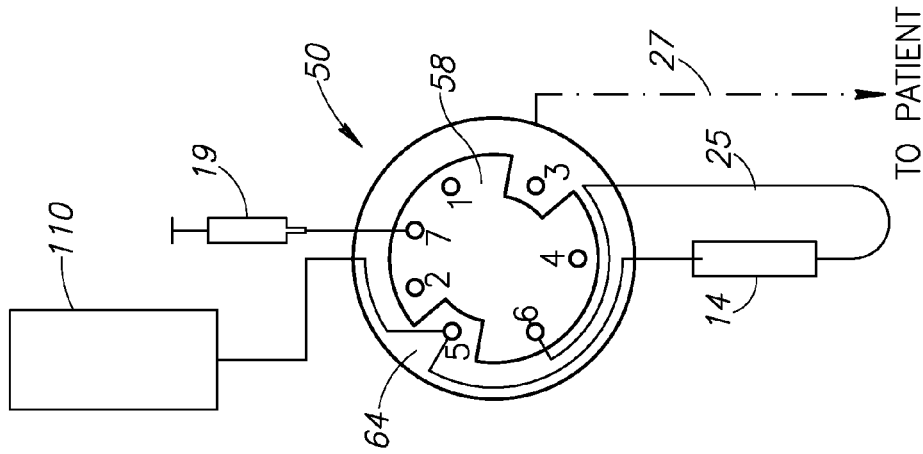
FIGS. 9A, 9B, 9C and 9D are schematic illustrations of the fluid flow for each of a treatment, priming, venting and sterilization states, respectively.
Figure 9B:
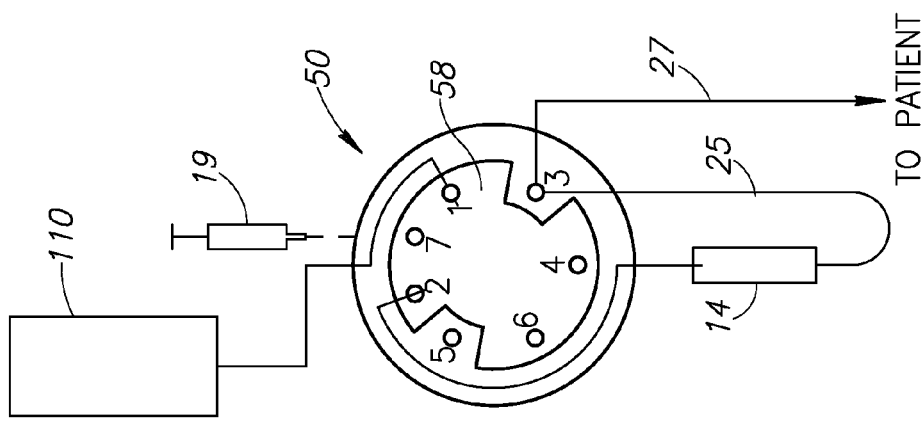
Figure 9A:
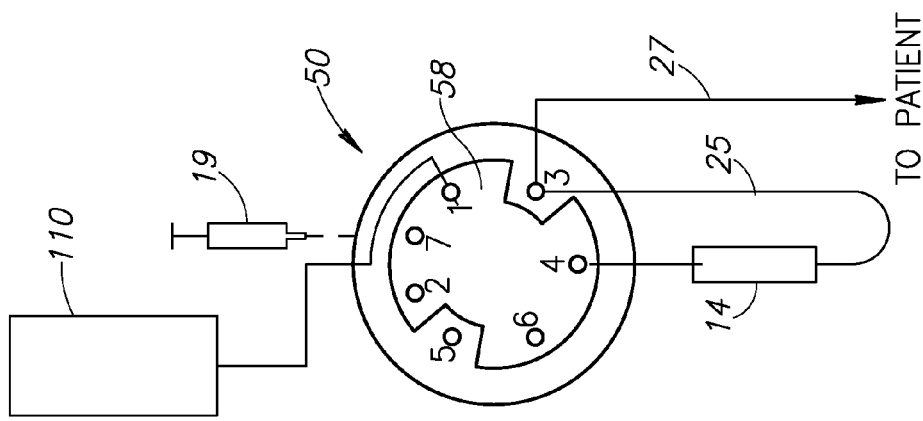
Figure 9D:
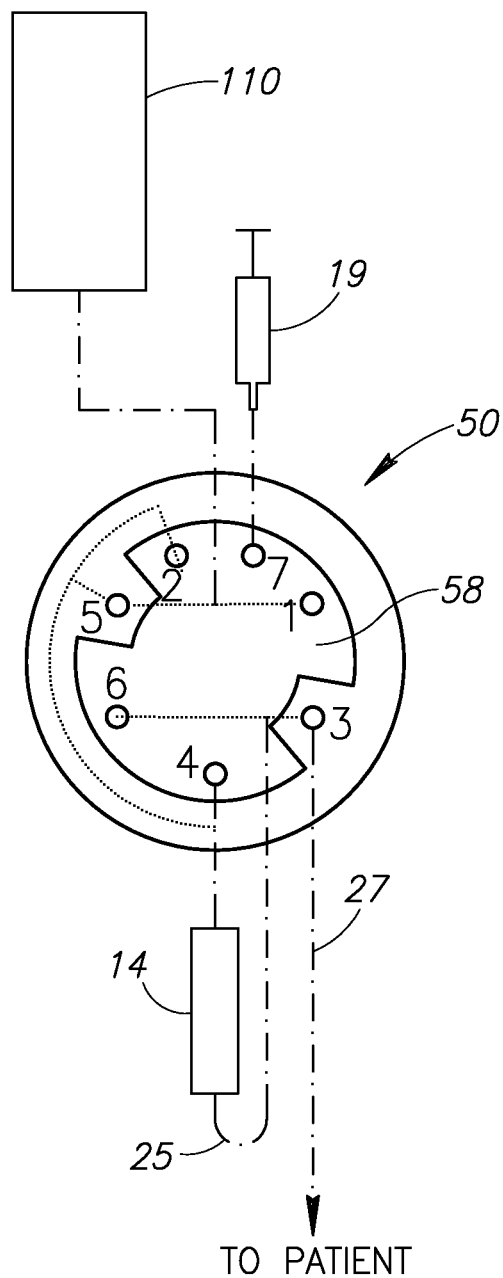

During priming, as shown in FIG. 9B, fluid flows from fluid bag 110, to supply valve 1, through chamber 58 to upper valve 2, through set interface 14 and return line 25 to patient valve 3 and from there to patient line 27.

During venting (FIG. 9C), fluid flows from fluid bag 110 to bypass valve 5 to bypass path 64 to set interface 14, to return line 25 into chamber 58 via return valve 6. Air vents through venting valve 7 and into syringe 19. Patient valve 3 is closed.

In the optional sterilization mode (FIG. 9D), typically used during assembly, all valves 1-7 are open to allow sterilization air to circulate through all of the tubing, air chamber 58, and all manifolds and conduits.

Figure 10A:
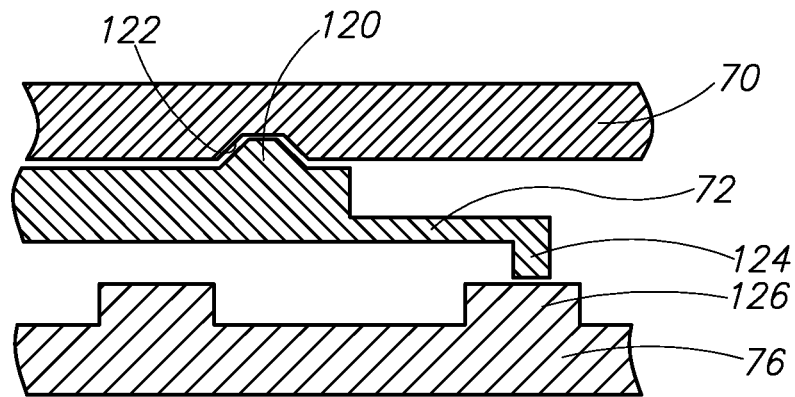
FIGS. 10A and 10B are schematic illustrations of elements of the air trap module of FIG. 3 utilized in manufacture and, in particular, for the sterilization mode during manufacture.
Figure 10B:
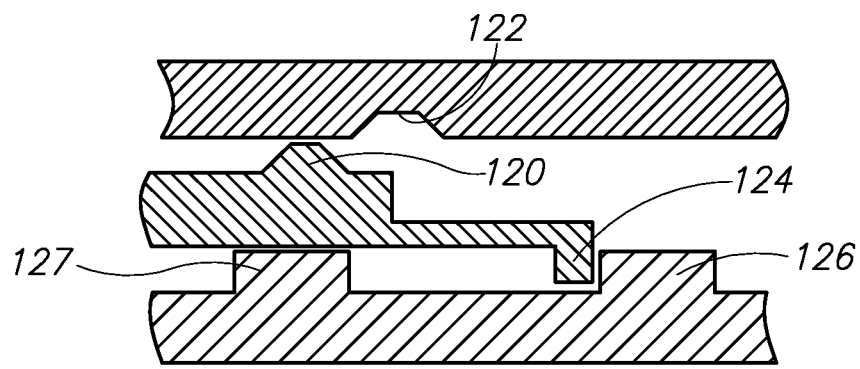

As shown in FIGS. 10A and 10B, to which reference is now briefly made, dial 72 may have a protrusion 120 that, during assembly, may be aligned with an assembly recess 122 in top cover 70. Moreover, dial 72 may have a flexible snap edge 124 which may be aligned, also during assembly, on top of an operating range edge 126 in hive 76.

In an alternative embodiment, protrusion 120 may be part of cover 70 and assembly recess 122 may be part of dial 72.

Typically, air trap module 50 may remain in the sterilization mode until first use, at which point the user may switch the dial to one of the operating modes. When this happens, dial 72 may move out of assembly recess 122, resulting in snap edge 124 moving off of operating range edge 126 and into an operating range defined by range edge 126 and another range edge 127. The described mechanism prevents switching the air trap module back to ETO mode once the user has switched it to one of the other operational modes (e.g. treatment, priming or venting). However, it is possible to overcome this restriction, particularly to test the module during assembly.

It will be appreciated that the embodiment of FIGS. 3-10 may be exemplary; other embodiments may be envisioned and are incorporated within the present invention. For example, each valve in the air trap module may have its own electro mechanical actuator. In this embodiment, the actuators may be connected to a microcontroller which may be located in the module or in the pump. The microcontroller may control the valves in a predefined manner, such as that described hereinabove or in accordance with any other manner or as programmed by a user.

In an alternative embodiment, the electro mechanical valve actuators may have a linear or rotary construction.

The electro mechanical valve actuators may be assembled in a separate assembly that may be snapped onto the air trap module. It may be constructed for multiple uses and may also have a secondary, manual actuator for when the electro mechanical actuator is not working. In this embodiment, the pump may control the operation of the air trap module and may activate the various valves according to the modes discussed hereinabove. The air detector of the pump may detect the presence of air and may control the valves to change from the treatment to venting and back. It may also control the priming state. In this embodiment, the air trap module may have 7 or 4 valves, as desired.

In one embodiment, during venting, the pump may drive an amount of fluid that is equivalent to the volume of air trap chamber 50 plus a small amount. This is a safety feature to prevent the pump from pushing the piston of the syringe out and spilling the medicine if the nurse forgets to stop the pump operation. The small amount is provided in case a small pressure is built up in the syringe, to ensure that all the air is removed. If the syringe is stuck, a pressure detector of the pump will alert of the pressure build up.

On the other hand, for a small syringe (5-10 ml), the pressure to start moving it may require a higher pressure. For example, it typically requires 1-2 levels of pressure to start the air drive to the syringe and a lower level of pressure to continue to drive it.

If desired, the pump may require the medical staff to input the volume of the syringe or collecting bag, typically prior to the first air removal. The pump may then alert the medical staff after the total air removed (over the course of a few removals) may reach the syringe volume.

Finally, air trap module 50 may include a syringe holder to physically block the syringe from jumping out of vent 18 if the pump operation was not stopped in time and resulted in an over flow.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An intravenous system comprising:
   a set interface configured to be mounted upon an intravenous pump such that a pumping action of said intravenous pump acts upon fluid contained within said set interface, pumping the fluid from an input of said set interface to an output of said set interface;
   a separate air trap connectable to said set interface, said air trap comprising:
      (a) an air chamber capable of receiving fluids and air,
      (b) a supply connection to receive a supply line,
      (c) a set interface connection connectable to the input of said set interface and configured to facilitate transfer of fluid from said air trap to said set interface,
      (d) an air vent,
      (e) a lower valve configured to control flow of fluid from said air chamber to said input of said set interface through said set interface connection,
      (f) a bypass line connecting said supply connection to said set interface connection, bypassing said air chamber, and
      (g) a bypass valve configured to control flow of fluid through said bypass line;
   a return line connecting the output of said set interface to said air chamber and to an outgoing patient line and including one or more return valves configured to control flow of fluid from the output of said set interface to either flow: (i) into said air chamber, or (ii) into an outgoing patient line, based on a state of said return valves; and
   actuators to control a state of said valves to enable: (i) a venting mode in which said return valves direct fluid from the output of said set interface to said air chamber, said lower valve prevents flow of fluid from said air chamber to said input of said set interface and said bypass valve directs fluid to flow through said bypass line; and (ii) a treatment mode in which said return valves direct fluid from the output of said set interface to the outgoing patient line said lower valve directs flow of fluid from said air chamber to said input of said set interface and said bypass valve prevents flow of fluid through said bypass line.

2. The system according to claim 1, further comprising a venting valve adapted to control flow of air out of said air chamber.

3. The system according to claim 2, wherein said venting valve includes a syringe connection adapted to facilitate an airtight connection between said air chamber and a syringe when said venting valve is open.

4. The system according to claim 3, wherein said actuators are further adapted to open all of said valves during a sterilization mode.

5. The system according to claim 1, further comprising a controller and wherein said actuators comprise one or more electro mechanical actuators controlled by said controller.

6. The system according to claim 5, wherein said controller causes said actuators to change between modes based on signals received from a bubble detector.

7. The system according to claim 2, wherein said actuators are further adapted to open said venting valve during the venting mode.

8. The system according to claim 1, further comprising a supply valve configured to control flow of fluid from said supply connection into said air chamber and wherein said actuators control said supply valve to: (1) direct fluid from said supply connection to said air chamber in the treatment mode and (2) prevent flow of fluid from said supply connection to said air chamber in the venting mode.

9. The system according to claim 1, further comprising an upper valve configured to control flow of fluid from an upper portion of said air chamber to said input of said set interface through said set interface connection and wherein said actuators are further adapted to control all of said valves to enable a priming state wherein said upper fluid valve, near the top of said air chamber, is open.

10. The system according to claim 1 including:
a venting valve to control the flow of air out of said air chamber;
a patient valve controlling flow into said patient line; and
an upper fluid valve, near the top of said air chamber.

11. An airtrap for an intravenous system, said airtrap comprising:
an air chamber capable of receiving fluids and air;
a supply connection to receive a supply line;
a set interface connection connectable to an input of a set interface, the set interface being configured to connect to an intravenous pump such that the pump applies a pumping action to the set interface, wherein the pumping action pumps fluid from the input of the set interface to an output of the set interface;
an air vent;
a lower valve configured to control flow of fluid from said air chamber to said input of said set interface through said set interface connection;
a bypass line connecting said supply connection to said set interface connection, bypassing said air chamber;
a bypass valve configured to control flow of fluid through said bypass line;
a return line connecting the output of said set interface to said air chamber and to an outgoing patient line and including one or more return valves configured to control flow of fluid from the output of said set interface to either flow: (i) into said air chamber, or (ii) into an outgoing patient line, based on a state of said return valves; and
actuators to control a state of said valves to enable: (i) a venting mode in which said return valves direct fluid from the output of said set interface to said air chamber, said lower valve prevents flow of fluid from said air chamber to the input of the set interface and said bypass valve directs fluid to flow through said bypass line; and (ii) a treatment mode in which said return valves direct fluid from the output of said set interface to the outgoing patient line said lower valve directs flow of fluid from said air chamber to the input of the set interface and said bypass valve prevents flow of fluid through said bypass line.

12. The airtrap according to claim 11, wherein said air chamber holds 2-4 ml.

13. The airtrap according to claim 11, further comprising a venting valve adapted to control flow of air out of said air chamber.

14. The airtrap according to claim 13, wherein said actuators are further adapted to open said venting valve during the venting mode.

15. The airtrap according to claim 13, wherein said venting valve includes a syringe connection adapted to facilitate an airtight connection between said air chamber and a syringe when said venting valve is open.

16. The airtrap according to claim 15, wherein said actuators are further adapted to open all of said valves during a sterilization mode.

17. The airtrap according to claim 11, further comprising a supply valve configured to control flow of fluid from said supply connection into said air chamber and said actuators control said supply valve to: (1) direct fluid from said supply connection to said air chamber in the treatment mode and (2) prevent flow of fluid from said supply connection to said airchamber in the venting mode.

18. An airtrap for an intravenous system, said airtrap comprising:
an air chamber capable of receiving fluids and air;
a supply connection to receive a supply line;
a set interface connection connectable to an input of a set interface, the set interface being configured to connect to an intravenous pump such that the pump applies a pumping action to the set interface and the pumping action pumps fluid from the input of the set interface to an output of the set interface;
an air vent;
a lower valve configured to control flow of fluid from said air chamber to the input of the set interface through said set interface connection;
a bypass line connecting said supply connection to said set interface connection, bypassing said air chamber;
a bypass valve configured to control flow of fluid through said bypass line;
a return line connecting the output of the set interface to said air chamber and to an outgoing patient line and including one or more return valves configured to control flow of fluid from the output of the set interface to either flow: (i) into said air chamber, or (ii) into an outgoing patient line, based on a state of said return valves;
and
actuators to control a state of said valves.

19. The airtrap according to claim 18, wherein said air chamber holds 2-4 ml.

20. The airtrap according to claim 18, further comprising a venting valve adapted to control flow of air out of said air chamber.

* * * * *